(12) United States Patent
Nandwana et al.

(10) Patent No.: US 11,298,430 B2
(45) Date of Patent: Apr. 12, 2022

(54) MAGNETIC NANOCOMPOSITE COMPOSITIONS

(71) Applicant: Northwestern University, Evanston, IL (US)

(72) Inventors: Vikas Nandwana, Evanston, IL (US); Vinayak P. Dravid, Glenview, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/587,973

(22) Filed: Sep. 30, 2019

(65) Prior Publication Data
US 2020/0101177 A1   Apr. 2, 2020

Related U.S. Application Data

(60) Provisional application No. 62/739,475, filed on Oct. 1, 2018.

(51) Int. Cl.
| | | |
|---|---|---|
| *A61B 5/055* | (2006.01) | |
| *A61K 49/18* | (2006.01) | |
| *C04B 35/26* | (2006.01) | |
| *C04B 35/628* | (2006.01) | |
| *H01F 1/00* | (2006.01) | |

(52) U.S. Cl.
CPC ...... *A61K 49/1827* (2013.01); *C04B 35/2658* (2013.01); *C04B 35/62826* (2013.01); *H01F 1/0018* (2013.01); *C04B 2235/3272* (2013.01); *C04B 2235/3274* (2013.01); *C04B 2235/5454* (2013.01); *C04B 2235/95* (2013.01)

(58) Field of Classification Search
None
See application file for complete search history.

(56) References Cited

U.S. PATENT DOCUMENTS

| | | |
|---|---|---|
| 8,945,628 B2 | 2/2015 | Weissleder et al. |
| 2003/0082237 A1 | 5/2003 | Cha et al. |
| 2003/0203865 A1 | 10/2003 | Harvie et al. |
| 2013/0034599 A1 | 2/2013 | Thaxton et al. |
| 2013/0315831 A1 | 11/2013 | Shi et al. |
| 2015/0182461 A1 | 7/2015 | Kim |
| 2015/0231282 A1 | 8/2015 | Pozzo et al. |
| 2016/0211062 A1 | 7/2016 | Granger et al. |
| 2017/0367982 A1 | 12/2017 | Nandwana et al. |
| 2019/0091154 A1 | 3/2019 | Nandwana et al. |
| 2020/0170946 A1 | 6/2020 | Dravid et al. |

OTHER PUBLICATIONS

Nikolic et al. (Mater. Letters 2014, 120, 86-89).*
Hong et al. (J. Alloys Compd. 2009, 480, 947-953).*
Perumbilavil et al. (Small 2018, 14, 1701001, p. 1-9).*
The International Search Report and Written Opinion issued in International Patent Application No. PCT/US18/34442 dated Aug. 23, 2018, pp. 1-9.
Yang, Xiao-Chao, et al. "Drug Delivery Using Nanoparticle-Stabilized Nanocapsules," *Angewandte Chemie International Edition* 50.2 (2011): 477-481.
Tao, Youhua, et al. "Reduction-responsive gold-nanoparticle-conjugated Pluronic micelles: an effective anti-cancer drug delivery system." *Journal of Materials Chemistry* 22.36 (2012): 18864-18871.
Bica et al., Sterically stabilized water based magnetic fluids: Synthesis, structure and properties. Journal of Magnetism and Magnetic Materials Apr. 2007; 311(1):17-21.
Cormode et al., Atherosclerotic plaque composition: analysis with multicolor CT and targeted gold nanoparticles. Radiology. Sep. 2010;256(3):774-82.
Cormode et al., Nanocrystal core high-density lipoproteins: a multimodality contrast agent platform. Nano Lett. Nov. 2008;8(11):3715-23.
Damiano et al., Templated high density lipoprotein nanoparticles as potential therapies and for molecular delivery. Adv Drug Deliv Rev. May 2013;65(5):649-62.
Fay et al., Nanocrystal Core Lipoprotein Biomimetics for Imaging of Lipoproteins and Associated Diseases. Curr Cardiovasc Imaging Rep. Feb. 1, 2013;6(1):45-54.
Fayad et al., Recombinant HDL-like nanoparticles: a specific contrast agent for MRI of atherosclerotic plaques. J Am Chem Soc. Dec. 22, 2004;126(50):16316-7.
Fournier et al., HDL phospholipid content and composition as a major factor determining cholesterol efflux capacity from Fu5AH cells to human serum. Arterioscler Thromb Vase Biol. Nov. 1997;17(11):2685-91.
Frias et al., Properties of a versatile nanoparticle platform contrast agent to image and characterize atherosclerotic plaques by magnetic resonance imaging. Nano Lett. Oct. 2006;6(10):2220-4.
Frullano et al., Multimodal MRI contrast agents. J Biol Inorg Chem. Sep. 2007;12(7):939-49.
Hung et al., Mechanisms of Gadographene-Mediated Proton Spin Relaxation. J Phys Chem C. 2013;117(31):16263-73.
Ingram et al., Superparamagnetic nanoclusters coated with oleic acid bilayers for stabilization of emulsions of water and oil at low concentration. J Colloid Interface Sci. Nov. 1, 2010;351(1):225-32.
Lan et al., Synthesis of bilayer oleic acid-coated Fe3O4 nanoparticles and their application in pH-responsive Pickering emulsions. J Colloid Interface Sci. Jun. 1, 2007;310(1):260-9.
Marrache et al., Biodegradable synthetic high-density lipoprotein nanoparticles for atherosclerosis. Proc Natl Acad Sci U S A. Jun. 4, 2013;110(23):9445-50.
Matosziuk et al., Structural optimization of Zn(II)-activated magnetic resonance imaging probes. Inorg Chem. Nov. 4, 2013;52(21):12250-61.

(Continued)

*Primary Examiner* — Michael G. Hartley
*Assistant Examiner* — Melissa J Perreira
(74) *Attorney, Agent, or Firm* — Bell & Manning, LLC

(57) ABSTRACT

Superparamagnetic nanocomposites are provided. In an embodiment, a superparamagnetic nanocomposite comprises a superparamagnetic core comprising a first, soft superparamagnetic ferrite and a superparamagnetic shell comprising a second, soft superparamagnetic ferrite, the shell formed over the core, wherein the first and second soft superparamagnetic ferrites are different compounds and have different magnetocrystalline anisotropies.

11 Claims, 18 Drawing Sheets

(56) References Cited

OTHER PUBLICATIONS

Skajaa et al., The biological properties of iron oxide core high-density lipoprotein in experimental atherosclerosis. Biomaterials. Jan. 2011;32(1):206-13.

Thaxton et al., Templated spherical high density lipoprotein nanoparticles. J Am Chem Soc. Feb. 4, 2009;131 (4):1384-5.

Yetukuri et al., Composition and lipid spatial distribution of HDL particles in subjects with low and high HDL-cholesterol. J Lipid Res. Aug. 2010;51(8):2341-51.

Zhang et al., "Detection and Treatment of Atherosclerosis Using Nanoparticles," Wiley Interdiscip rev Nanomed Nanobiotechnol. Jan. 2017: 9(1): Doi:10.1002/wnan.1412, pp. 1-39.

Xie et al., "Enhanced Soft Magnetic Properties of Iron-Based Powder Cores with Co-Existence of $Fe_3O_4$—$MnZnFe_2O_4$ Nanoparticles," Metals, 2018, vol. 8, 702. pp. 1-11.

Nandwana et al., "Engineered Theranostic Magnetic Nanostructures: Role of Composition and Surface Coating on Magnetic Resonance Imaging Contrast and Thermal Activation," ACS Appl. Mater. Interfaces, 2016, vol. 8, pp. 6953-6961.

Nandwana et al., "High-Density Lipoprotein-like Magnetic Nanostructures (HDL-MNS): Theranostic Agents for Cardiovascular Disease," Chem. Mater., 2017, vol. 29, pp. 2276-2282.

Lee et al., "Artificially engineered magnetic nanoparticles for ultra-sensitive molecular imaging," Nature Medicine, Jan. 2007, vol. 13, No. 1, pp. 95-99.

Jang et al., "Critical Enhancements of MRI Contrast and Hyperthermic Effects by Dopant-Controlled Magnetic Nanoparticles**," Angew. Chem., 2009, vol. 121, pp. 1260-1264.

Anupana Bhat et al., "Effects of gold nanoparticles on lipid packing and membrane pore formation," *Appl. Phys. Lett.*, (2016), vol. 109; 263106; pp. 1-6.

* cited by examiner

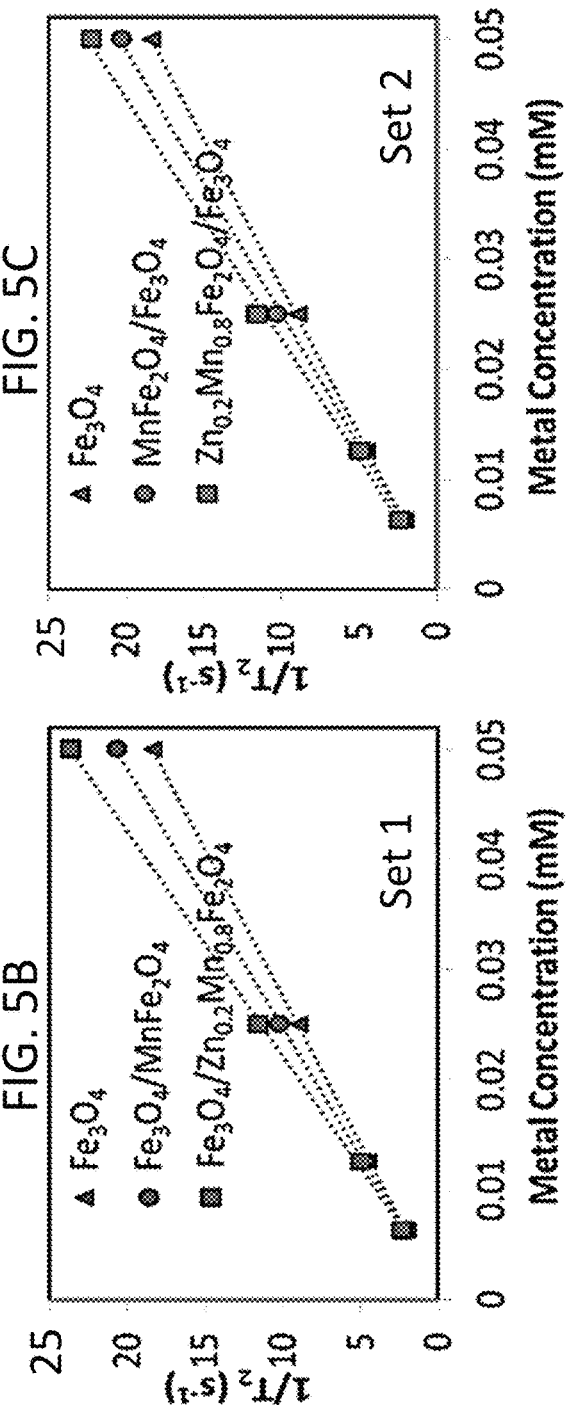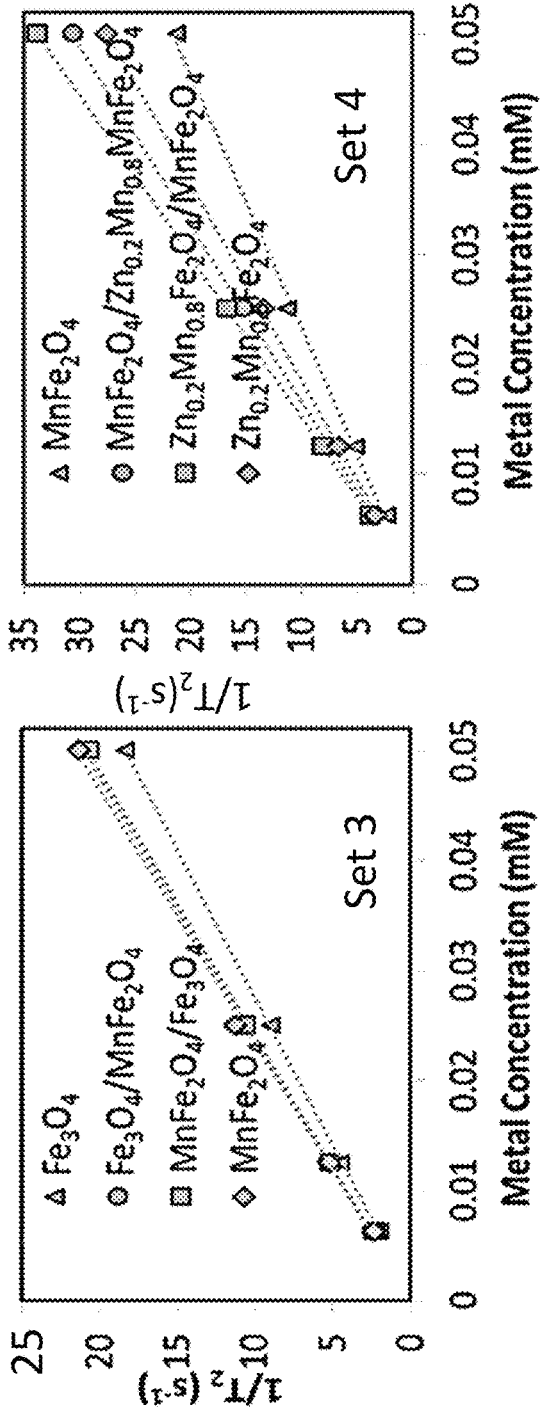
FIG. 5B  FIG. 5C  FIG. 5E  FIG. 5F

MAGNETIC NANOCOMPOSITE COMPOSITIONS

CROSS-REFERENCE TO RELATED APPLICATIONS

The present application claims priority to U.S. provisional patent application No. 62/739,475 that was filed Oct. 1, 2018, the entire contents of which are incorporated herein for reference.

BACKGROUND

Exchange coupling between hard and soft magnetic materials at the nanoscale leads to improved physical properties for energy and data storage applications. Exchange coupling has also been explored in core/shell magnetic nanostructures (MNS) composed of hard and soft magnetic spinel ferrites, but applications have been limited in biomedicine due to the presence of 'toxic' cobalt based ferrites as hard magnetic components.

SUMMARY

Provided are nanocomposites, compositions comprising the nanocomposites, and methods of using the nanocomposites and nanocomposite-based compositions.

In one aspect superparamagnetic nanocomposites are provided. In an embodiment, a superparamagnetic nanocomposite comprises a superparamagnetic core comprising a first, soft superparamagnetic ferrite and a superparamagnetic shell comprising a second, soft superparamagnetic ferrite, the shell formed over the core, wherein the first and second soft superparamagnetic ferrites are different compounds and have different magnetocrystalline anisotropies.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

(FIGS. 2A-2B) At RT, both set samples showed superparamagnetic behavior. (FIGS. 2C-2D) At 10K, hysteresis was observed in both set samples, demonstrating ferromagnetic nature.

(FIGS. 3A-3B) In sets 1 and 2, the shell (or core) was changed from $Fe_3O_4$ to $MnFe_2O_4$ and $Zn_{0.2}Mn_{0.8}Fe_2O_4$, and magnetic susceptibility increased. (FIGS. 3C-3D) In sets 3 and 4, core/shell MNS showed higher magnetic susceptibility than their single-phase counterparts.

FIGS. 5A-5F show a comparison of $r_2$ relaxivity (FIGS. 5A and 5D) values and corresponding plots (FIGS. 5B, 5C, 5E, and 5F) of set 1 ($Fe_3O_4$, $Fe_3O_4/MnFe_2O_4$, $Fe_3O_4/Zn_{0.2}Mn_{0.8}Fe_2O_4$), set 2 ($Fe_3O_4$, $MnFe_2O_4/Fe_3O_4$, $Zn_{0.2}Mn_{0.8}Fe_2O_4/Fe_3O_4$), set 3 $Fe_3O_4$, $MnFe_2O_4$, $Fe_3O_4/MnFe_2O_4$, $MnFe_2O_4$, $F_3O_4$), and set 4 ($MnFe_2O_4$, $Zn_{0.2}Mn_{0.8}Fe_2O_4$, $MnFe_2O_4/Zn_{0.2}Mn_{0.8}Fe_2O_4$, $Zn_{0.2}Mn_{0.8}Fe_2O_4/MnFe_2O_4$) samples. In sets 1 and 2, the shell (or core) was changed from $Fe_3O_4$ to $MnFe_2O_4$, and $Zn_{0.2}Mn_{0.8}Fe_2O_4$, and $r_2$ relaxivity increased.) In sets 3 and 4, core/shell MNS showed higher $r_2$ relaxivity than their single-phase counterparts.

DETAILED DESCRIPTION

Provided are nanocomposites, compositions comprising the nanocomposites and methods of using the nanocomposites and nanocomposite-based compositions.

In one aspect, nanocomposites are provided. In an embodiment, a nanocomposite comprises a core comprising (or consisting essentially of or consisting of) a first, soft magnetic ferrite and a shell comprising (or consisting essentially of or consisting of) a second, soft magnetic ferrite, the shell formed over the core. The first and second soft magnetic ferrites are chemical compounds which are different front one another. In addition, the first and second soft magnetic ferrites have different magnetocrystalline anisotropies from one another. The phrase "soft magnetic" is used to distinguish such compounds/materials from "hard magnetic" compounds/materials. A soft magnetic compound/material has a magnetocrystalline anisotropy that is less than that of a hard magnetic compound/material. Although the first and second magnetic ferrites have different magnetocrystalline anisotropies from one another, the values of the anisotropies will both be less than those of hard magnetic compounds/ materials. Hard magnetic materials have magnetocrystalline anisotropies on the order of $10^7$ J/m$^3$. By way of illustration, the magnetocrystalline anisotropies of several hard magnetic materials are as follows: CoCrPt=0.20×$10^7$ J/m$^3$, Co=0.45× $10^7$ Co$_3$Pt=2×$10^7$ J/m$^3$, FePd=1.8×$10^7$ J/m$^3$, FePt=6.6–10× $10^7$ J/m$^3$, CoPt=4.9×$10^7$ J/m$^3$, MnAl=1.7×$10^7$ J/m$^3$, Fe$_{14}$Nd$_2$B=4.6×$10^7$ J/m$^s$, SmCo$_5$=11–20×$10^7$ J/m$^3$. By contrast, soft magnetic materials have magnetocrystalline anisotropies on the order of $10^4$ J/m$^3$. By way of illustration, the magnetocrystalline anisotropies of several soft magnetic materials is as follows: Fe$_3$O$_{4=11\times10^4}$ J/m$^3$, MnFe$_2$O$_{4=3\times10^4}$ J/m$^3$, NiFe$_2$O$_{4=6.2\times10^4}$ J/m$^3$, MgFe$_2$O$_{4=2.5\times10^4}$ J/m$^3$. Thus, the magnetocrystalline anisotropies (Ku) of the first and second magnetic ferrites may be $10^5$ J/m$^3$ or less, $10^4$ J/m$^3$ or less, $10^3$ J/m$^3$ or less, or in the range of from $10^5$ to $10^3$ J/m$^3$.

Due to their different magnetocrystalline anisotropies, the first and second soft magnetic ferrites can undergo exchange coupling in the nanocomposite. The existence of exchange coupling may be confirmed by measuring magnetization-field (M-H) loops and zero-field cooling (ZFC) curves as described in the Example, below. Specifically, an absence of a kink in an M-H loop measured at 10 K is an indication of an exchange-coupled core-shell. Similarly, the existence of a single peak in an ZFC plot measured at 100 Oe is an indication of an exchanged-coupled core-shell.

Figure 8:
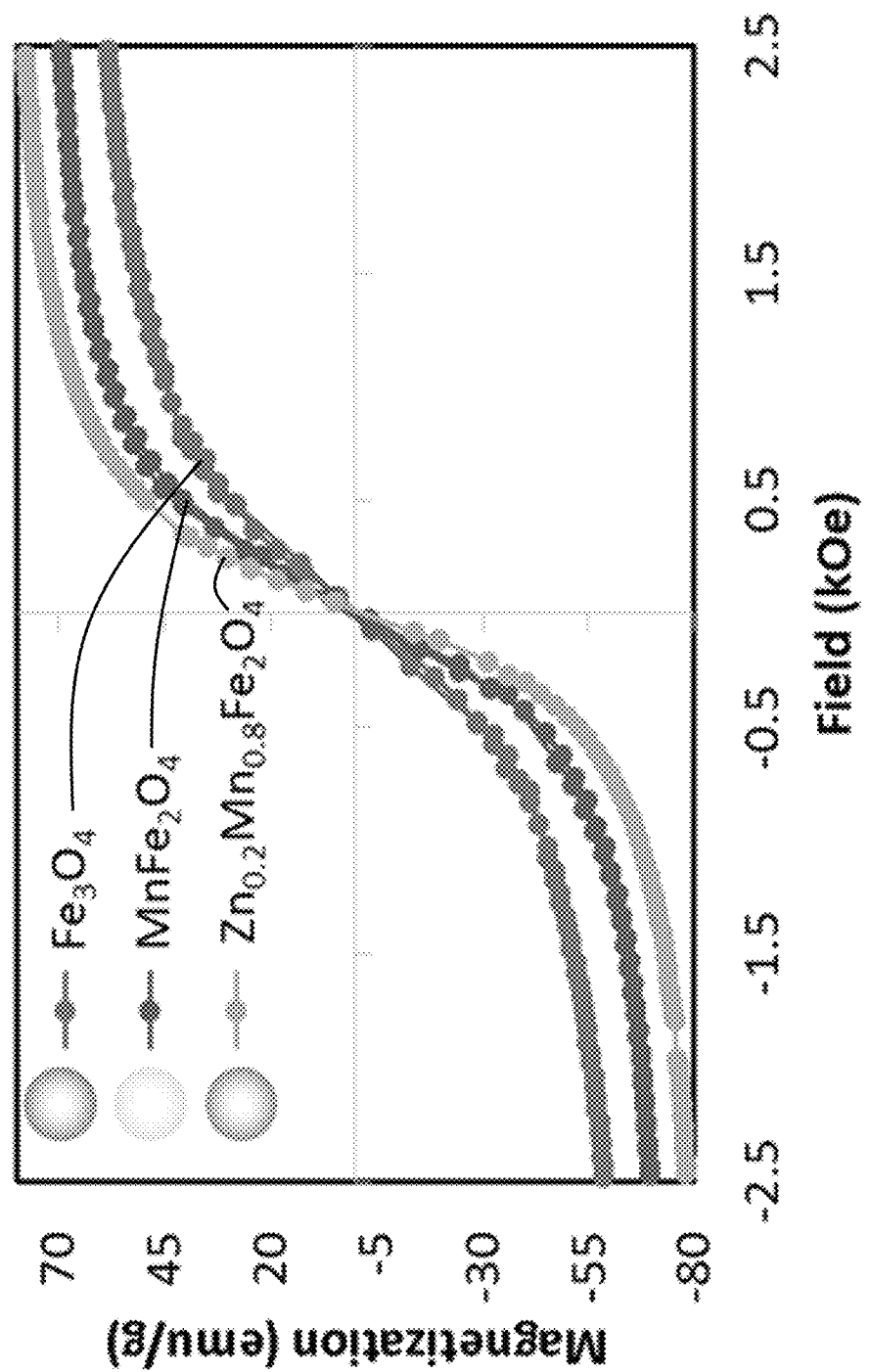
FIG. 8 shows magnetization-Field (M-H) loops of $Fe_3O_4$, $MnFe_2O_4$, and $Zn_{0.2}Mn_{0.8}Fe_2O_4$ samples at RT demonstrating that both set samples show superparamagnetic behavior. $Zn_{0.2}Mn_{0.8}Fe_2O_4$ demonstrate highest saturation magnetization while $Fe_3O_4$ show the lowest.

The soft magnetic ferrite compounds used for the core and shell of the nanocomposite are superparamagnetic. This means that a magnetization-field (M-H) loop measured from a sample of nanoparticles composed of the ferrite compound and having an average diameter of 12 nm exhibits no hysteresis at room temperature (20 to 25° C.). Such M-H loops are shown in FIG. 8. To confirm superparamagnetic behavior, samples may be prepared and M-H loops may be measured as described in the Example, below. "Superparamagnetic" also means that the sample of nanoparticles composed of the ferrite compound and having the average diameter of 12 nm also exhibits a single-peaked ZFC plot having a blocking temperature (as determined from the single-peaked ZFC plot) that is less than room temperature. Again, samples may be prepared, ZFC plots measured, and blocking temperatures determined as described in the Example, below.

Figure 2A:
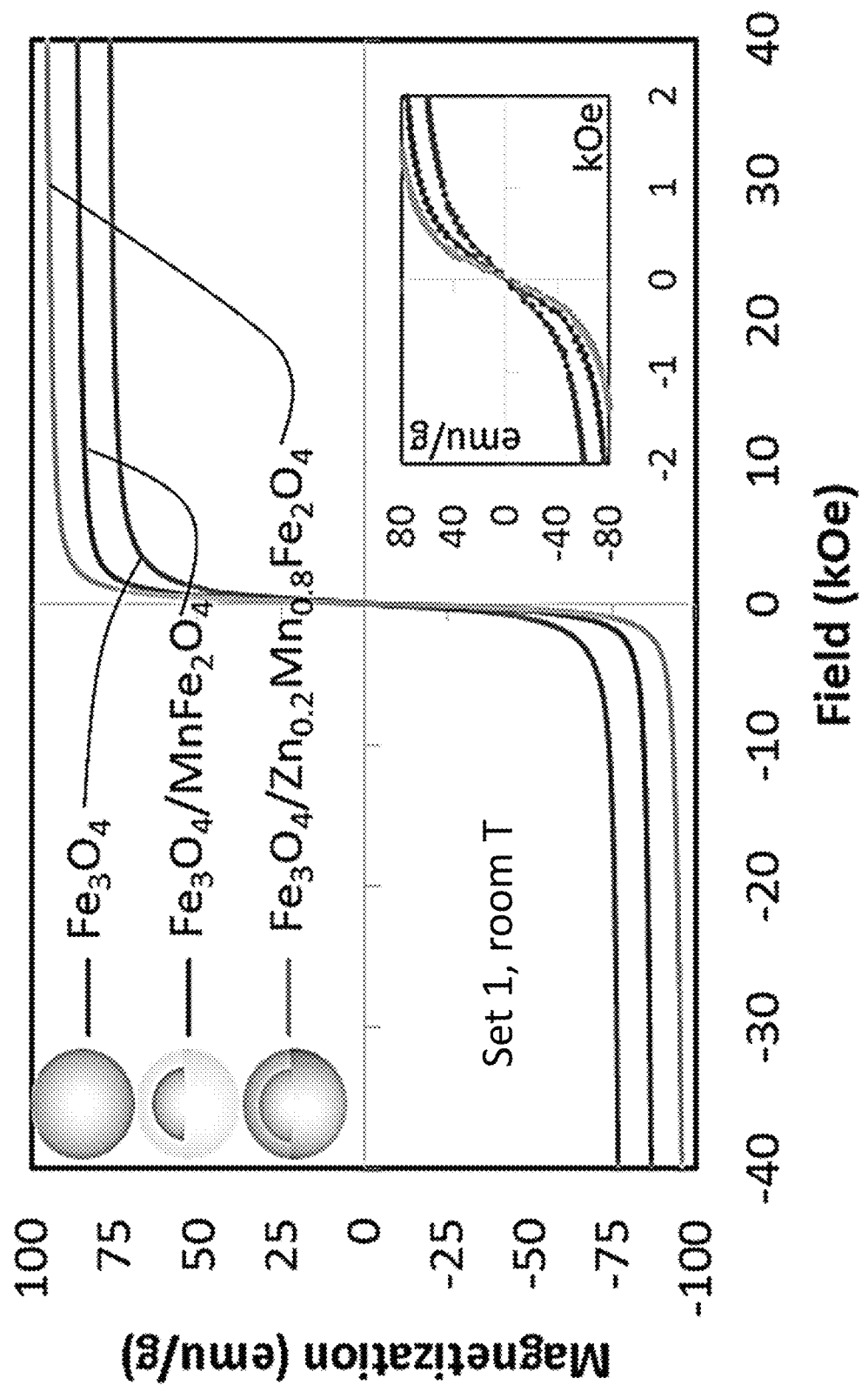
FIGS. 2A-2D show magnetization-field (M-I-I) loops of set 1 ($Fe_3O_4$, $Fe_3O_4/MnFe_2O_4$, $Fe_3O_4/Zn_{0.2}Mn_{0.8}Fe_2O_4$) and set 2 ($Fe_3O_4$, $MnFe_2O_4/Fe_3O_1$, $Zr_{0.2}Mn_{0.8}Fe_2O_4/Fe_3O_4$) samples at room temperature (RT) and 10K.
Figure 2B:
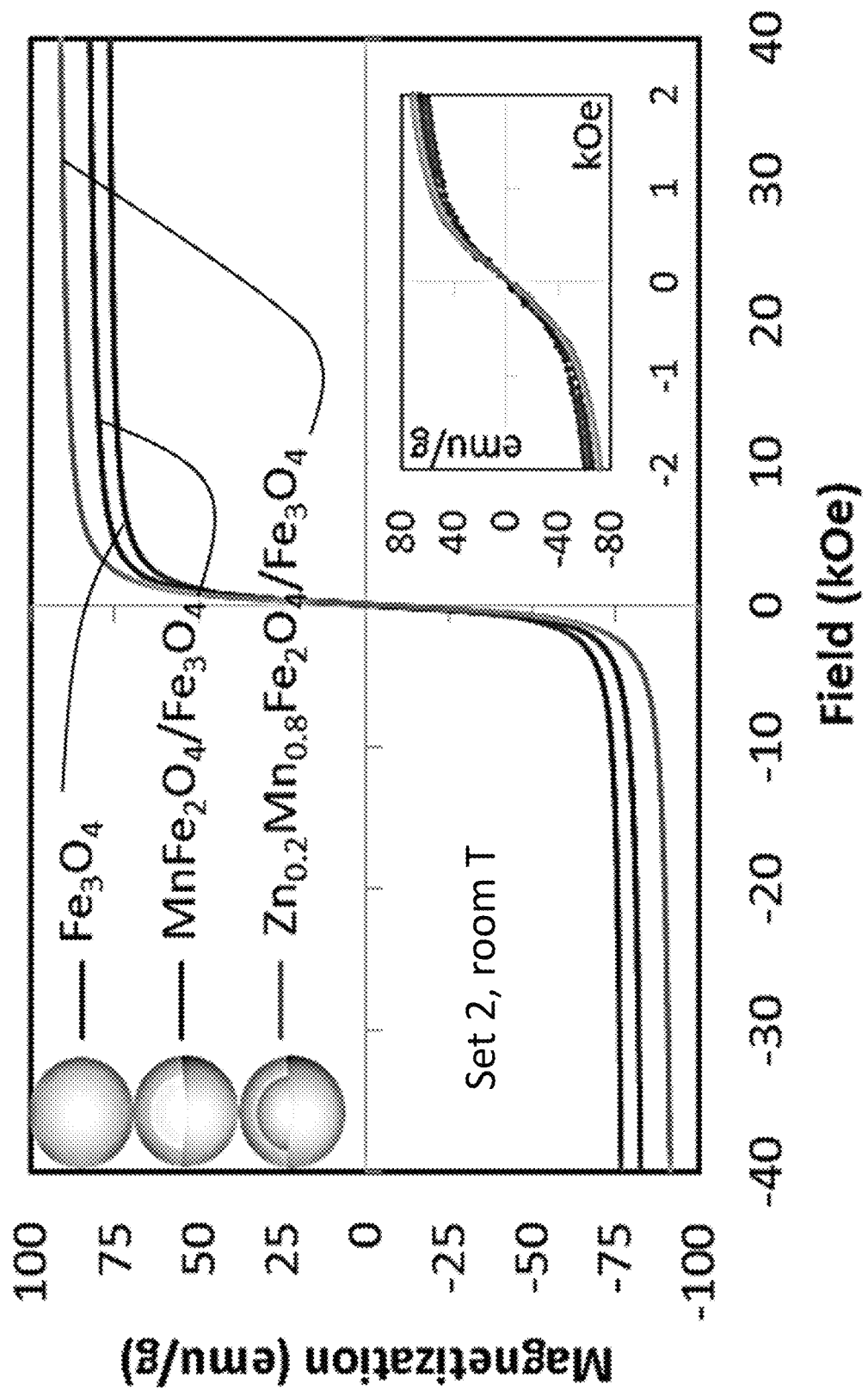
Figure 4A:
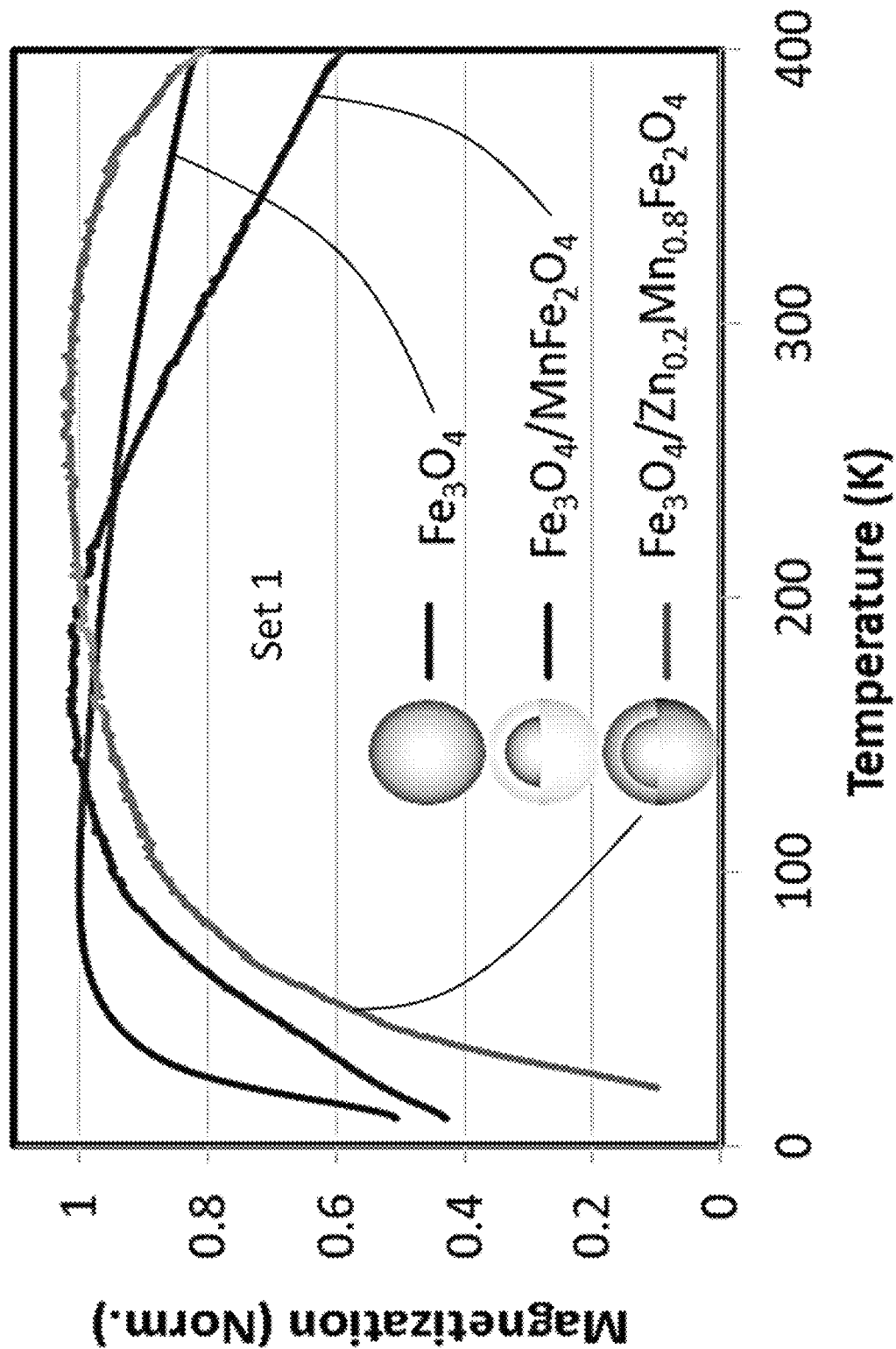
FIGS. 4A-4B show zero-field cooling (ZFC) curves of (FIG. 4A) set 1 ($Fe_3O_4$, $Fe_3O_4/MnFe_2O_4$, $Fe_3O_4/Zn_{0.2}Mn_{0.8}Fe_2O_4$) and (FIG. 4B) set 2 ($Fe_3O_4$, $MnFe_2O_4/Fe_3O_4$, $Zn_{0.2}Mn_{0.8}Fe_2O_4/Fe_3O_4$) samples. When the shell (or core) was changed from $Fe_3O_4$ to $MnFe_2O_4$ and $Zn_{0.2}Mn_{0.8}Fe_2O_4$, blocking temperature increased for both sets.
Figure 4B:
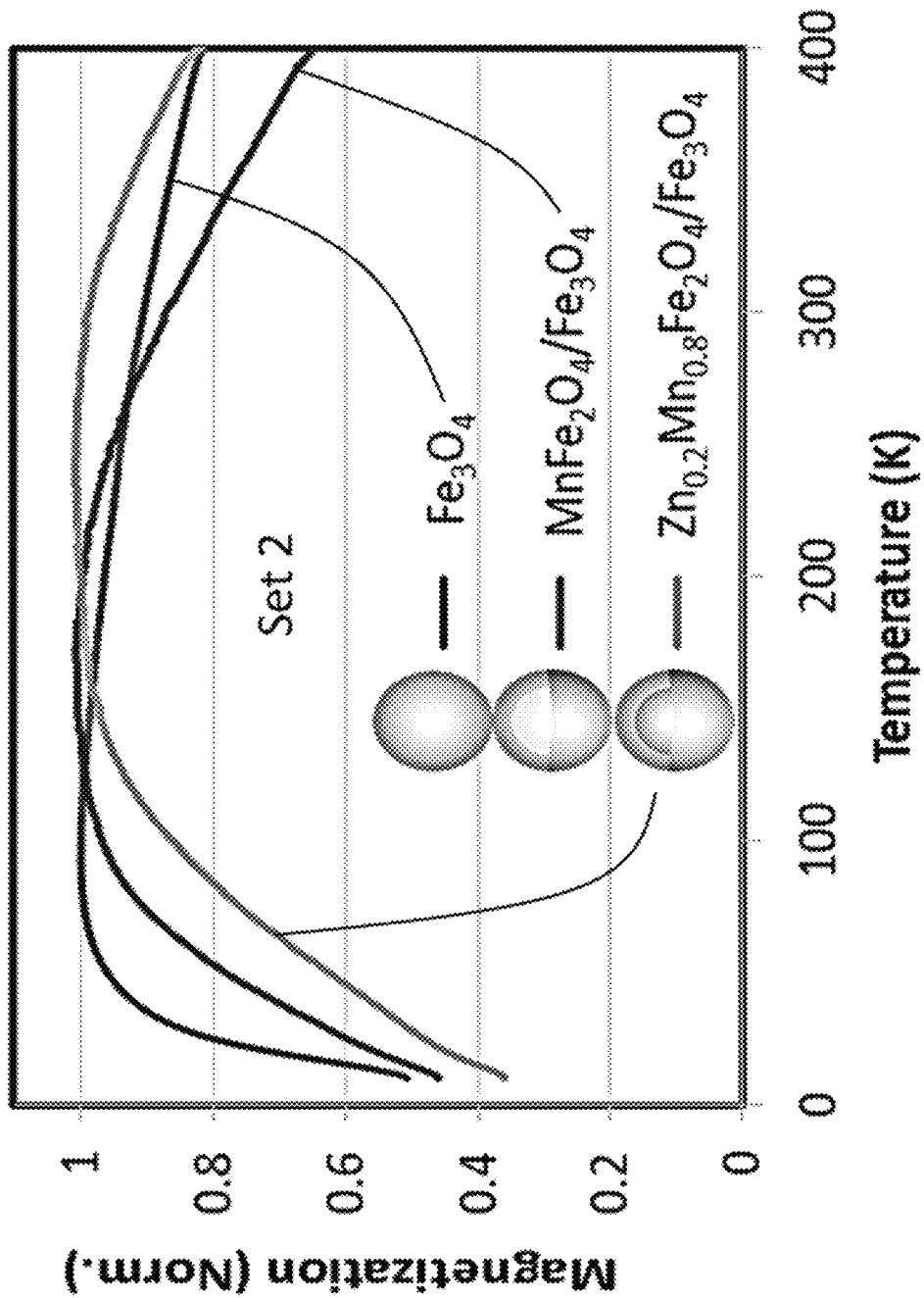

As a result, the core, shell, and nanocomposite thus formed from such soft, superparamagnetic ferrite compounds may also be referred to herein as superparamagnetic. The superparamagnetic behavior of the core, shell, and nanocomposite is also demonstrated, e.g., from FIGS. 2A, 2B showing M-H loops at room temperature measured from a sample of 12 nm nanoparticles (core or core/shell) composed of the soft, superparamagnetic ferrite compounds as indicated thereon. The M-H loops exhibit no hysteresis. The superparamagnetic behavior of the core, shell, and nanocomposite is also demonstrated, e.g., from FIGS. 4A, 4B showing single-peaked ZFC plots for the same 12 nm nanoparticles having blocking temperatures less than room temperature.

The superparamagnetic nature of the soft magnetic ferrite compounds used to form the cores and shells of the present nanocomposites thus distinguishes nanocomposites formed from ferromagnetic cores and superparamagnetic shells such as those disclosed in U.S. Pat. No. 8,945,628. As described in U.S. Pat. No. 8,945,628, the nanocomposite cores are required to be formed from ferromagnetic materials which exhibit hysteresis and remanence (or remnant magnetization) at room temperature in loops and double-peaked ZFC curves showing the core blocking temperature to be greater than room temperature.

Various soft magnetic ferrite compounds may be used for the core and shell of the nanocomposite, provided they achieve the superparamagnetic behavior described above. The soft magnetic ferrite compounds may have a spinel crystal structure, i.e., AB$_2$O$_4$. Illustrative soft magnetic ferrite compounds include Fe$_3$O$_4$, MnFe$_2$O$_4$, NiFe$_2$O$_4$, MgFe$_2$O$_4$, ZnFe$_2$O$_4$, Zn$_x$Mn$_{1-x}$Fe$_2$O$_4$(x=0.1 to 0.9), Mn$_x$Ni$_{1-x}$Fe$_2$O$_4$(x=0.1 to 0.9), Ni$_x$Zn$_{1-x}$Fe$_2$O$_4$(x=0.1 to 0.9), Mg$_x$Ni$_{1-x}$Fe$_2$O$_4$(x=0.1 to 0.9), Mg$_x$Zn$_{1-x}$Fe$_2$O$_4$(x=0.1 to 0.9), Mg$_x$Mn$_{1-x}$Fe$_2$O$_4$ (x=0.1 to 0.9). In embodiments, the soft magnetic ferrite compound has a formula M'$_x$M"$_{1-x}$Fe$_2$O$_4$, wherein M' and M" are different and are independently selected from Mn, Ni, Mg, and Zn and 0≤x≤1. In some such embodiments, 0.1≤x≤0.9. The nanocomposites generally do not contain any significant amount (i.e., an amount which affects the magnetic properties of the nanocomposite or a measurable amount) of Co, Pt, Nd, and Sm. Thus, the present nanocomposites are cheaper, more environmentally friendly, more chemically stable and more readily scalable compared to conventional exchange-coupled nanocomposites.

An individual nanocomposite may be characterized by its overall dimensions (i.e., the core and the shell formed thereover) and its shape. The nanocomposite may have each of its dimensions (i.e., 3) on the order of about 100 nm or less. These dimensions may be of similar magnitude to one another. Such nanocomposites may be referred to as nanoparticles. The nanoparticles may be spherical, but this term also encompasses irregularly shaped particles which are still reasonably well defined by a sphere. This term also encompasses particles which may have one or more flat facets, e.g., nanocubes. Nanoparticle shaped nanocomposites may be characterized by an average diameter which may be about 100 tun or less, about 50 nm or less, about 25 nm or less, about 15 nm or less, about 10 nm or less, or in the range of from about 1 nm to about 100 nm. By "average" it is meant an average value as determined from a representative number of individual nanocomposites in a sample.

The nanocomposite may have other overall dimensions and shapes. By way of illustration, a nanocomposite having two dimensions on the order of about 100 nm or less may be used, e.g., nanowires, nanorods, nanofibers, nanowhiskers, etc. A nanocomposite having one dimension on the order of about 100 nm or less may be used, e.g., nanosheets, nanoplates, nanoflakes, etc.

As noted above, the nanocomposite is a core-shell structure. The core itself may have dimensions and shapes including those described above with respect to the overall dimension/shape of the nanocomposite. The shell is a layer on, including in direct contact with, the outer surface of the core. This layer may completely cover the core. The shell may be characterized by an average thickness. By "average" it is meant an average value as determined from a representative number of nanocomposites in a sample. The shell generally has an average thickness which is less than the average nanoscale dimension of the core (e.g., the average diameter of a nanoparticle shaped core). In embodiments, the average thickness of the shell is about 50% or less, about 25% or less, about 15% or less, or about 10% or less than that of the average diameter of the core. Illustrative average thicknesses include 50 nm or less, 25 nm or less, 15 nin or less, 10 nm or less, 5 nm or less, or in the range of from about 1 nm to about 10 nm. The existence of the core-shell structure may be determined using electron energy loss spectroscopy (EELS) as described in the Example, below.

The nanocomposite may be characterized by a number of magnetic and theranostic properties. Regarding magnetic properties, e.g., the nanocomposite may be characterized by a saturation magnetization and a magnetic susceptibility. These properties may be measured from magnetization-field (M-H) loops and normalized magnetic susceptibility plots obtained as described in the Example, below. Regarding theranostic properties, e.g., the nanocomposite may be characterized by a $r_2$ relaxivity and a specific absorption rate (SAR). These properties may be measured from relaxation rate $R_2$ plots and thermal activation plots, respectively, obtained as described in the Example, below.

As described in the Example, below, the particular combination of first and second soft magnetic ferrites, the core dimensions and the shell thickness may be selected to time the magnetic and theranostic properties of the nanocomposite. By way of illustration, these parameters may be tuned to obtain a desired, e.g., maximum, $r_2$ relaxivity and/or a desired, e.g., maximum, SAR. In embodiments, the nanocotnposite is characterized by an $r_2$ relaxivity of at least 100 $mM^{-1}s^{-1}$, at least 250 $mM^{-1}s^{-1}$, at least 500 $mM^{-1}s^{-1}$, at least 600 $mM^{-1}s^{-1}$, at least 700 $nM^{-1}s^{-1}$, at least 1000 $mM^{-1}s^{-1}$ or in the range of from 100 $mM^{-1}s^{-1}$ to 1000 $mM^{-1}s^{-1}$. In embodiments, the nanocomposite is characterized by an SAR of at least 300 W/g, at least 600 W/g, at least 700 W/g, at least 800 W/g, at least 1000 W/gat least 1500 W/g, at least 2000 W/g, or in the range of from 300 W/g to 2500 W/g.

Figure 5A:
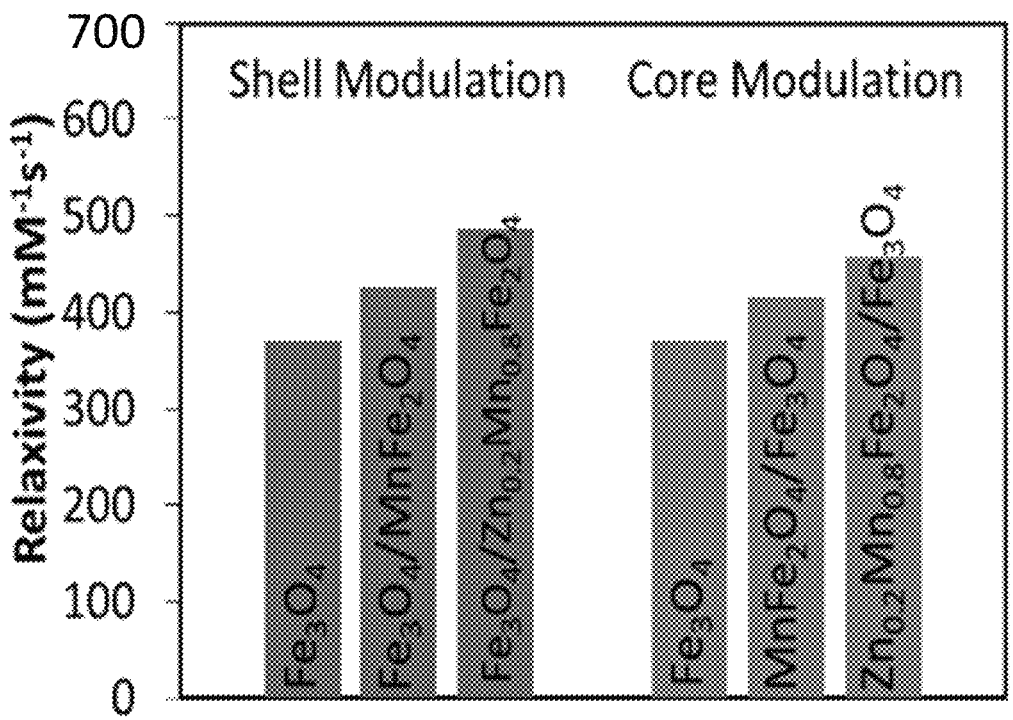
Figure 5D:
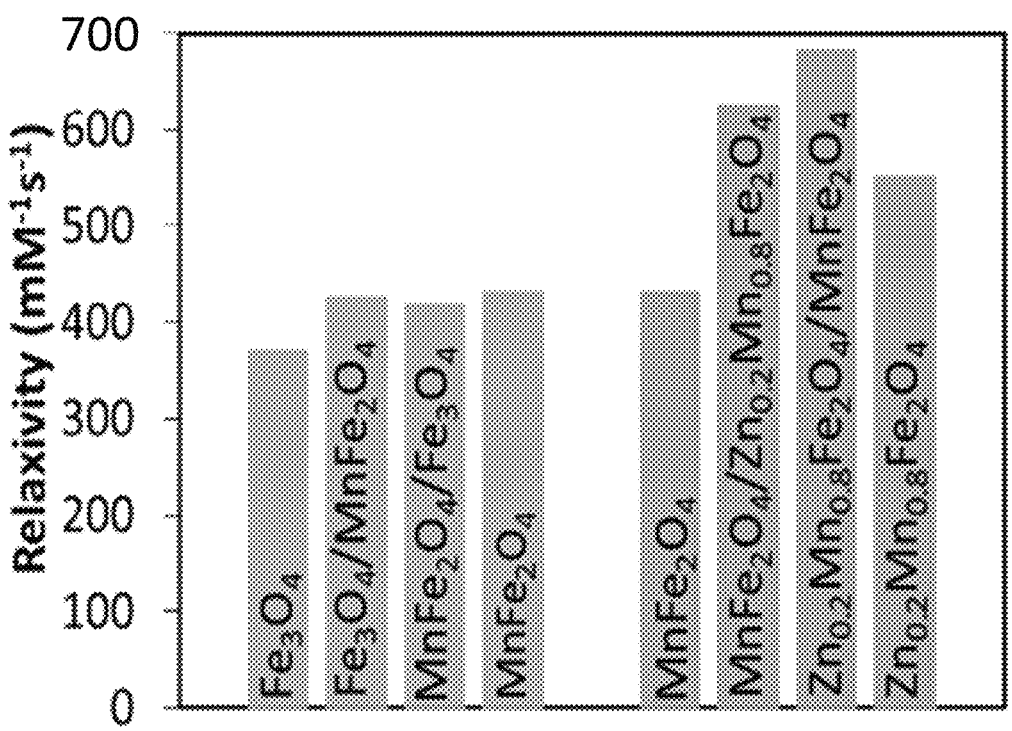
Figure 6A:
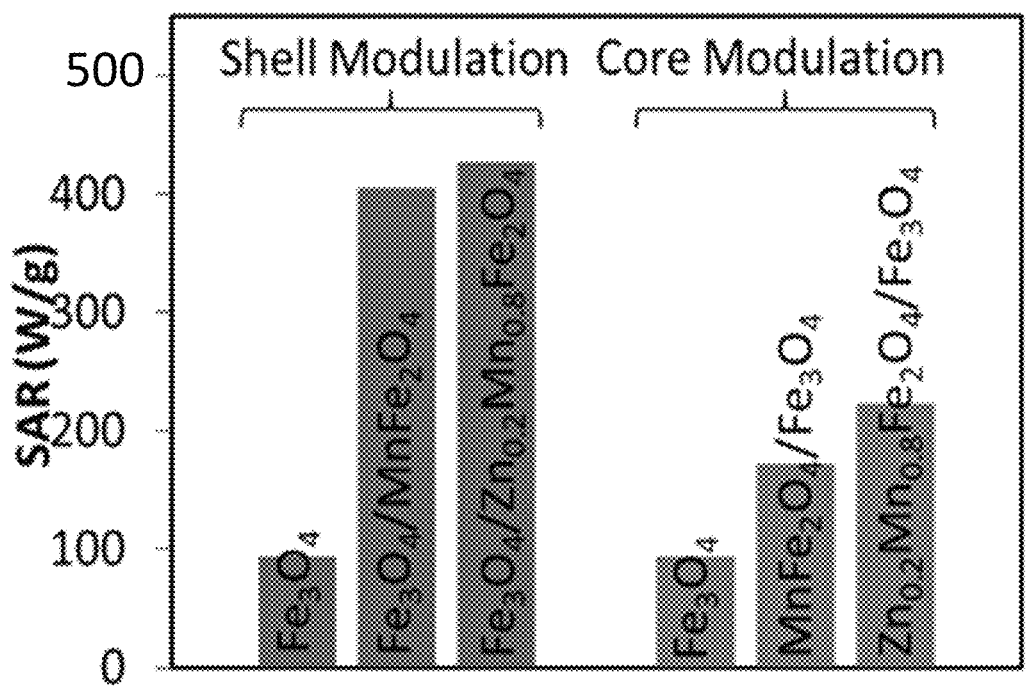
FIGS. 6A-6D show a comparison of (FIGS. 6A and 6D) specific absorption rate (SAR) values and (FIGS. 6B, 6C, 6E, and 6F) radio frequency (RF) field induced thermal activation plots of set 1 ($Fe_3O_4$, $Fe_3O_4/MnFe_2O_4$, $Fe_3O_4/Zn_{0.2}Mn_{0.8}Fe_2O_4$), set 2 ($Fe_3O_4$, $MnFe_2O_4/Fe_3O_4$, $Zn_{0.2}Mn_{0.8}Fe_2O_4/Fe_3O_4$), set 3 ($Fe_3O_4$, $MnFe_2O_4$, $Fe_3O_4/MnFe_2O_4$), and set 4 ($MnFe_2O_4$, $Zn_{0.2}Mn_{0.8}Fe_2O_4$, $MnFe_2O_4/Zn_{0.2}Mno.8Fe_2O_4$) samples. In sets 1 and 2, the shell (or core) was changed from $Fe_3O_4$ to $MnFe_2O_4$, and $Zn_{0.2}Mn_{0.8}Fe_2O_4$, and RF induced temperature as well as SAR increased. In sets 3 and 4, core/shell MNS showed higher RF induced temperature and SAR than their single-phase counterparts. The size of all MNS (single phase or core/shell) was 12 nm.
Figure 6D:
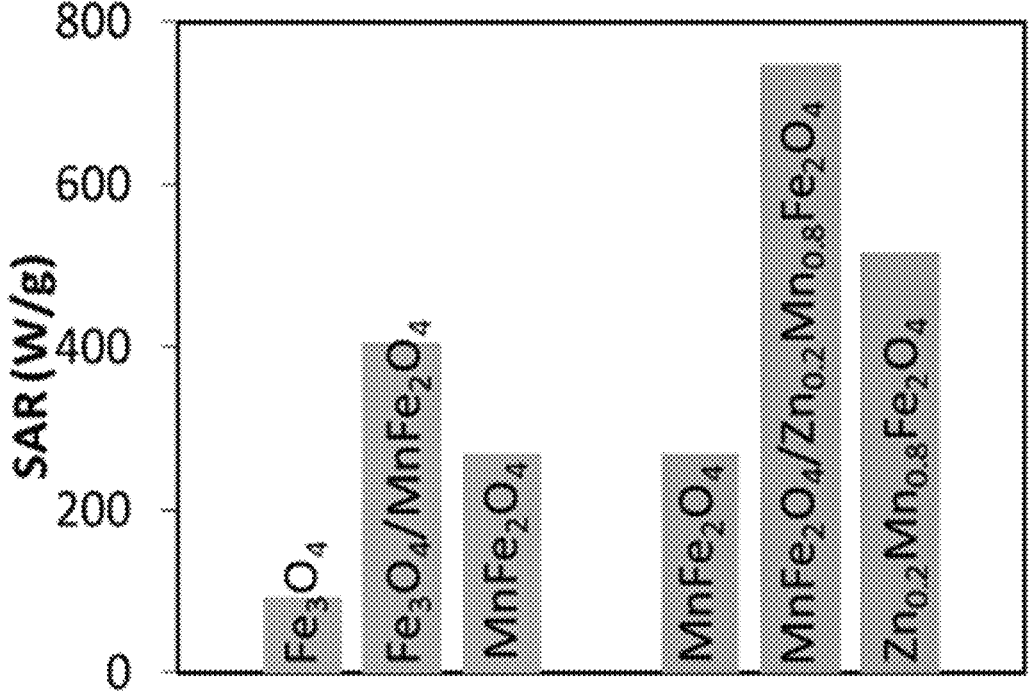
Figure 6C:
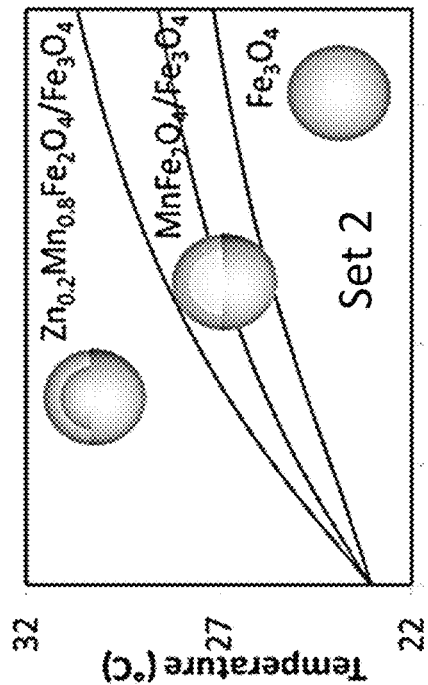
Figure 6F:
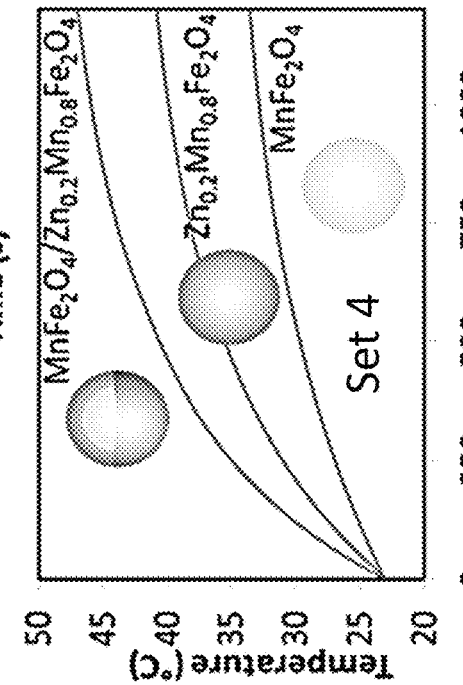
Figure 7A:
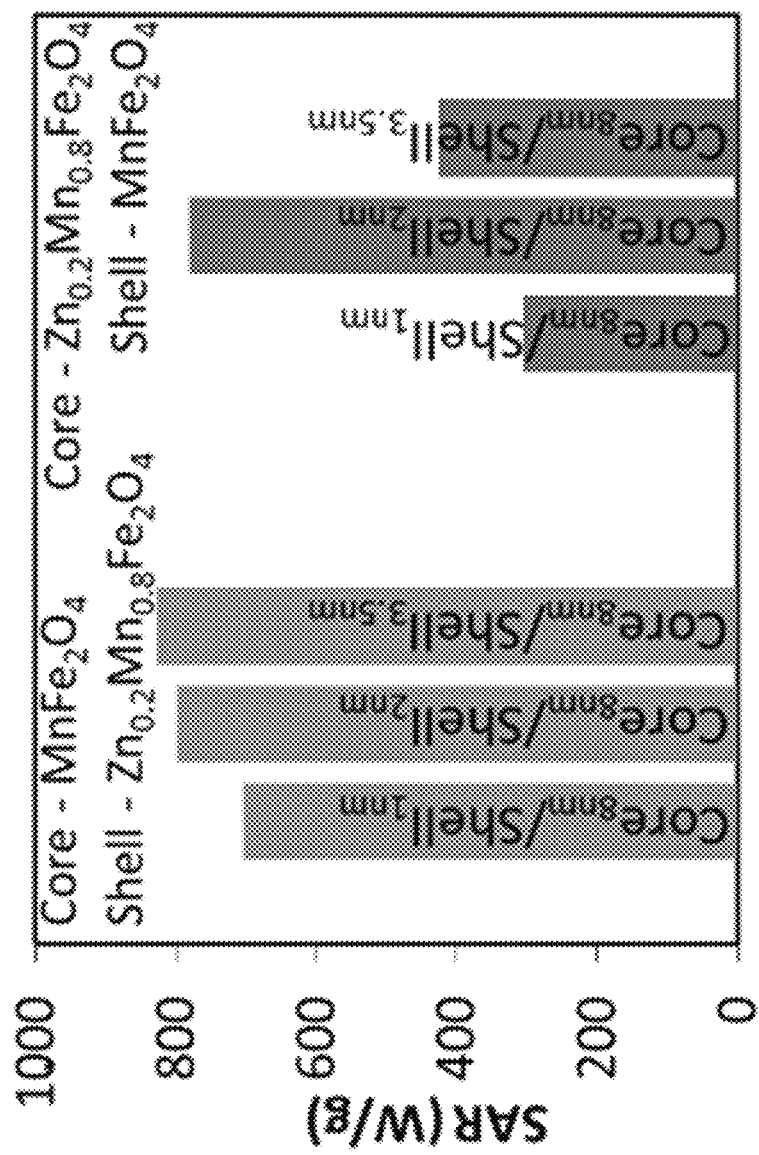
FIGS. 7A-7C show results from the optimization of thermal activation properties of core/shell MNS where core size was kept constant at 8 nm while the shell was tuned from 1 nm to 3.5 nm. SAR values (FIG. 7A) and thermal activation plots (FIGS. 7B and 7C) of $MnFe_2O_4/Zn_{0.2}Mn_{0.8}Fe_2O_4$ and $Zn_{0.2}Mn_{0.8}Fe_2O_4/MnFe_2O_4$ core/shell MNS show that exchange coupling is critically dependent on proportion and dimension of core and shell component in core/shell MNS.

Together FIGS. 5A, 5D, FIGS. 6A, 6D and FIG. 7A, demonstrate the unexpectedly superior effect the use of a soft, superparamagnetic shell has on both $r_2$ relaxivity and SAR when used in combination with a soft, superparamagnetic core. By way of illustration, superparamagnetic nanocomposites composed of the soft, superparamagnetic ferrites $MnFe_2O_4$ and $Zn_{0.2}Mn_{0.8}Fe_2O_4$ are described in detail in the Examples below. As shown in FIG. 7A, these superparamagnetic nanocomposites exhibit unexpectedly high SAR values, e.g., close to 800 W/g for core/shell. $Zn_{0.2}Mn_{0.8}Fe_2O_4/MnFe_2O_4$ and over 800 W/g for core/shell $MnFe_2O_4/Zn_{0.2}Mn_{0.8}Fe_2O_4$.

Any of the disclosed nanocomposites may be used in a variety of applications. Illustrative applications include biomedical applications such as non-invasive diagnostic imaging (e.g., nanocomposites as contrast agents in magnetic resonance imaging) and therapy; enhanced oil recovery by providing local heat generation; high energy permanent magnets; data storage via high density magnetic recording media; wastewater treatment including organic contaminant removal, oil removal, heavy metal removal; and energy storage via anode materials for lithium ion batteries. The nanocomposites may be provided as a composition comprising a plurality of the individual nanocomposites and a variety of other components, depending upon the particular application. By way of illustration, for biomedical applications, the nanocomposites may be combined with a carrier, such as a pharmaceutically acceptable liquid medium, for delivery to a patient or a tissue of a patient.

Methods of using the disclosed nanocomposites are also provided. By way of illustration, a method may comprise delivering any of the disclosed nanocomposites or nanocomposite-based compositions to a patient or a tissue of a patient and exposing the delivered nanocomposite to a magnetic field, e.g., a magnetic field generated by a magnetic resonance imaging system. Alternatively, the delivered nanocomposite may be exposed to an external radio frequency (RF) field, thereby thermally activating the nanocomposite to generate heat.

Methods of making the disclosed nanocomposites are provided in the Example, below.

EXAMPLE

Introduction

Figure 1:
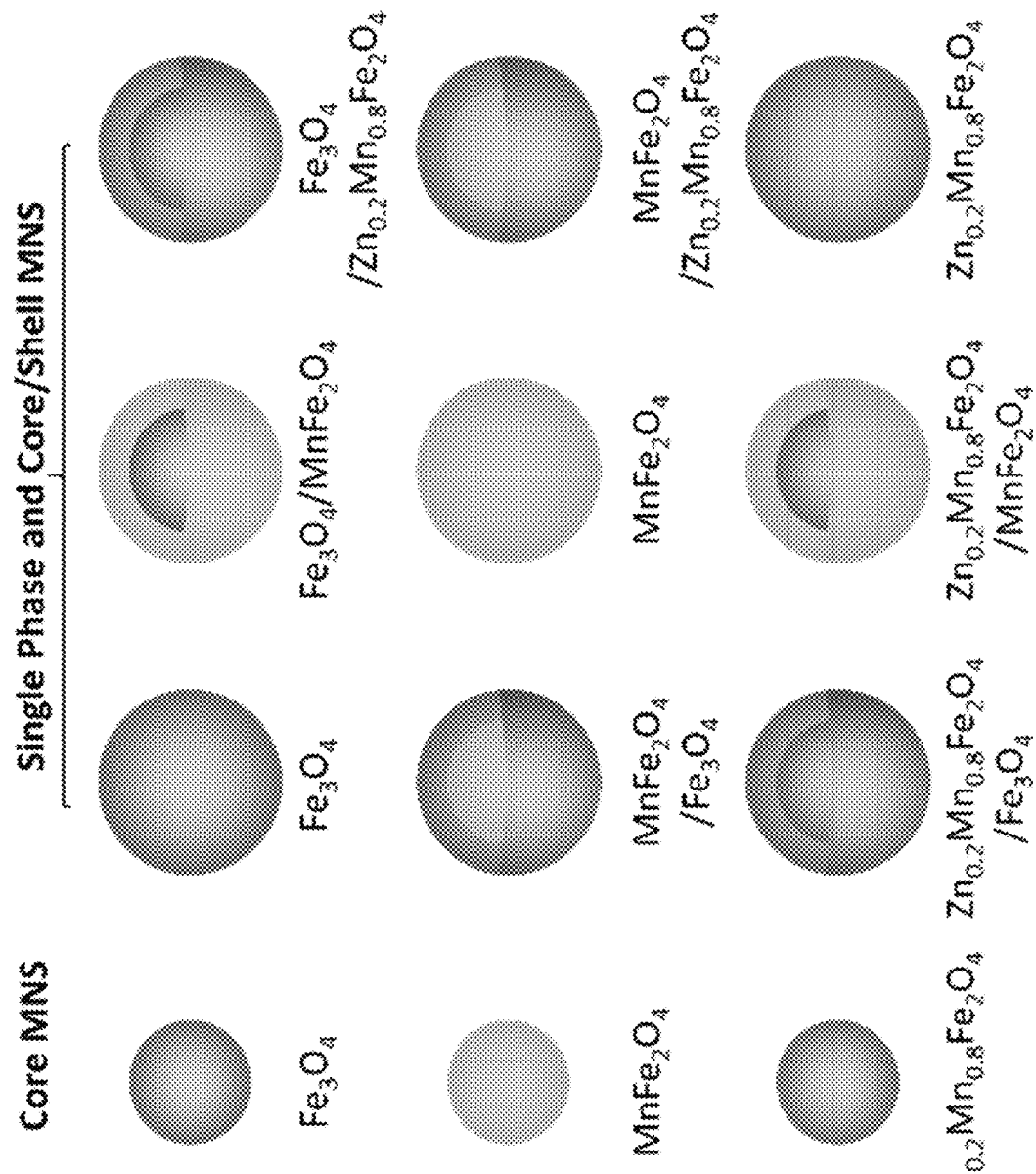
FIG. 1 shows a schematic of illustrative nanocomposites.

Here, exchange-coupled core/shell MNS composed of spinel ferrites are reported. $Fe_3O_4$, $MnFe_2O_4$, $Zn_{0.2}Mn_{0.8}Fe_2O_4$ were chosen as a core and/or shell MNS component (FIG. 1). Physical properties of core/shell MNS are compared with same size core or shell components (single phase MNS). This comparison avoids any size dependent effect and gives the direct effect of exchange coupling. Although all these ferrites are considered soft magnetic due to lower anisotropy ($K_u \sim 10^3$ $J/m^3$), using magnetic characterization, the exchange interactions between core and shell components have been shown to occur due to the difference in their anisotropy. Higher susceptibility and anisotropy of core/shell MNS have been observed compared to same size single phase MNS. Using relaxation and thermal activation plots, the increase in susceptibility and anisotropy has been shown to significantly improve contrast enhancement and thermal activation properties of core/shell MNS compared to the same size single phase MNS. The enhanced theranostic properties of MNS can also be further tuned by selection of core and shell components and their dimensions. Overall, the findings described here demonstrate the exchange coupling in soft and biocompatible MNS and present an alternative way to modulate theranostic properties of MNS for biomedical applications.

Experimental Details

Synthesis of Single Phase and Core/Shell Magnetic Nanostructures

The 8 nm $Fe_3O_4$, $MnFe_2O_4$, and $Zn_{0.2}Mn_{0.8}Fe_2O_4$ nanoparticles were synthesized using previously reported thermal decomposition methods. (Nandwana, V. et al., *Acs Appl Mater Inter* 2016, 8, 6953-6961; and Nandwana, V. et al., *Chem Mater* 2017, 29, 2276-2282.) Core/shell nanostructures were synthesized by a seed mediated approach for synthesis where the 8 nm $MFe_2O_4$ (M=Fe, Mn, $Zn_{0.2}Mn_{0.8}$) nanoparticles were used as seeds (labelled as core MNS) to grow a shell of the same or different material. For example, when $Fe_3O_4$ core MNS were used as seeds, addition of Mn and Mn+Zn precursor resulted in $Fe_3O_4/MnFe_2O_4$ and $Fe_3O_4/Zn_{0.2}Mn_{0.8}Fe_2O_4$ (labelled as core/shell MNS), respectively, while addition of Fe precursor resulted in larger size $Fe_3O_4$ (labelled as single phase MNS). A library of core/shell nanostructures was synthesized by combination of these three ferrites as core and shell components. In a typical $Fe_3O_4/MnFe_2O_4$ nanostructure synthesis, $Fe_3O_4$ NPs (25 mg as core NPs), $Fe(acac)_3$ (2 mmol), 1,2-hexadecanediol (10 mmol), oleic acid (6 mmol), oleylamine (6 mmol), and benzyl ether (20 mL) were charged in a 100 mL three-neck round-bottom flask and magnetically stirred under a flow of nitrogen. The mixture was first heated to 110° C. for 1 hour to remove moisture. Then the temperature was increased to 210° C. for 1 hour, and the mixture was finally refluxed for 1 hour before cooling down to room temperature. The black-brown mixture was precipitated, washed three times using ethanol, and was then dispersed in hexane. The composition was changed by choosing different precursors and their ratios. $Fe_3O_4/Zn_{0.2}Mn_{0.8}Fe_2O_4$ nanoparticles were synthesized by adding Mn(acac)$_2$ (2 mmol) and Zn(acac)$_2$ (1 mmol) under identical conditions.

Functionalization of Single Phase and Core/Shell Magnetic Nanostructures

To convert from hydrophobic to hydrophilic nature, the as-synthesized oleic acid coated hydrophobic core/shell (or single phase) MNS were functionalized with citrate via ligand exchange process, resulting in hydrophilic MNS. The particle diameters and size distribution were determined from transmission electron microscopy (TEM). The final concentration of the Fe, Mn, and Zn in MNS was determined by inductively coupled plasma mass spectrometry (ICP-MS) analysis.

Structural and Magnetic Characterization

The seed mediated growth was confirmed by TEM and energy dispersive x-ray (EDX) using Hitachi H8100 TEM (200 kV) and Hitachi HD2300 (200 kV), respectively. M-H hysteresis loops and field-cooled (FC)/ZFC magnetization curves were recorded using a physical property measurement system (Quantum Design Dyanacool-PPMS). The stoichiometry of core/shell and single phase MNS was confirmed via ICP-MS. To calculate saturation magnetization emu/g, mass of all metal (Fe and/or Zn and/or Mil) was considered which was calculated via ICP-MS. Additional TEM images, selected area electron diffraction (SAED) patterns, and EDX profiles were acquired using JEOL Grand ARM 300F TEM. HAADF STEM images and corresponding EELS profiles were obtained using a JEOL ARM 200F TEM.

Measurement of $r_2$ Relaxivity

MFe$_2$O$_4$ magnetic nanostructures dispersed in water were diluted to concentrations ranging from 0.01 to 0.11 mM of metal ion. $T_2$ relaxation times were determined at 3.0 T Magnetom Verio (Siemens Healthcare, Erlangen, Germany) using the multiple-echo-fast-spin-echo sequence with TR-1290 ins, 8 echo times starting with 9.9 to 79.2 ins, 160 mm FOV, 256×256 matrix, and slice thickness 3 mm. Given that there were multiple samples with a distribution of $T_2$ relaxation times, the range of echo times had to be limited, so the echo time range may not be optimal for every sample. A commercial 12 channel head coil (diameter~160 mm) was used. A 1.5 mL Eppendorf centrifuge tube was used as a sample holder. $R_2$ maps were generated using a custom software using Matlab. The signal decay was fit to a single exponential function to estimate $T_2$ on a pixel by pixel basis. To calculate $r_2$ relaxivity, mass of all metal (Fe and/or Zn and/or Mn) was considered which was calculated via ICP-MS.

Thermal Activation

Thermal activation experiments were performed on an MSI Automation Inc. Hyperthermia Research System RF generator at a frequency of 300 kHz and a power of 5 kW. A 0.2 mL suspension was placed inside the 5 cm coil generating the AC magnetic field of 5 kA/m. A nonmagnetic nonmetallic optical temperature probe (Fiso) was used to monitor the temperature. Each experiment time duration was 15 minutes. SAR was calculated from the thermal activation plots using the following equation $$SAR = \frac{CV_s}{m}\left(\frac{dT}{dt}\right) \quad (1)$$

where C is the specific heat capacity of the solvent, dT/dt is the initial slope of the thermal activation plat, Vs is the sample volume, and m is mass of magnetic material in the sample.

Results and Discussion

To synthesize core/shell MNS, Fe$_3$O$_4$, MnFe$_2$O$_4$, and Zn$_{0.2}$Mn$_{0.8}$Fe$_2$O$_4$ were selected for this study. The seed mediated approach for synthesis was used where MFe$_2$O$_4$ nanoparticles were used as seeds (labelled as core MNS) to grow shells of the same or different material. For example, when Fe$_3$O$_4$ core MNS were used as seeds, addition of Mn and Mn+Zn precursor resulted in Fe$_3$O$_4$/MnFe$_2$O$_4$ and Fe$_3$O$_4$/Zn$_{0.2}$Mn$_{0.8}$Fe$_2$O$_4$ (labelled as core/shell MNS), respectively, while addition of Fe precursor resulted in larger size Fe$_3$O$_4$ (labelled as single phase MNS). Similarly, MnFe$_2$O$_4$ and Zn$_{0.2}$Mn$_{0.8}$Fe$_2$O$_4$ core MNS were used as seeds to prepare a library of core/shell and single phase MNS (FIG. 1). For magnetic characterization (magnetization loops, anisotropy, and susceptibility) and theranostic characterization (contrast enhancement and thermal activation), the samples were divided into four sets. In set 1 samples, the core was kept constant as Fe$_3$O$_4$, while the shell was varied from Fe$_3$O$_4$ to MnFe$_2$O$_4$ and Zn$_{0.2}$Mn$_{0.8}$Fe$_2$O$_4$. In set 2, the Fe$_3$O$_4$ shell was kept constant, and the core was varied from Fe$_3$O$_4$ to MnFe$_2$O$_4$ and Zn$_{0.2}$Mn$_{0.8}$Fe$_2$O$_4$. In set 3, single phase Fe$_3$O$_4$ and MnFe$_2$O$_4$ MNS were compared with their core/shell counterparts, Fe$_3$O$_4$/MnFe$_2$O$_4$ or MnFe$_2$O$_4$/Fe$_3$O$_4$. In set 4, single phase MnFe$_2$O$_4$ and Zn$_{0.2}$Mn$_{0.8}$Fe$_2$O$_4$ MNS were compared with their core/shell counterparts, MnFe$_2$O$_4$/Zn$_{0.2}$Mn$_{0.8}$Fe$_2$O$_4$ or Zn$_{0.2}$Mn$_{0.8}$Fe$_2$O$_4$/MnFe$_2$O$_4$. The size of all core/shell and single phase MNS was kept constant to avoid any size effect on magnetic and theranostic properties.

The seed mediated growth was confirmed by TEM and EDX. The size of the core MNS was kept at 8 nm, while the size of the core/shell and the single phase MNS was kept at 12 nm. TEM images of 8 nm Fe$_3$O$_4$ core MNS, 12 nm Fe$_3$O$_4$ single phase MNS, 12 nm Fe$_3$O$_4$/MnFe$_2$O$_4$, and 12 nm Fe$_3$O$_4$/Zn$_{0.2}$Mn$_{0.8}$Fe$_2$O$_4$ core/shell MNS were obtained (not shown). The shell thickness was tuned by controlling the amount of core MNS during synthesis of the core/shell MNS while the amount of shell precursors was kept constant. The TEM images of the core/shell MNS do not show distinguished core and shell structures since the lattice mismatch and contrast between Fe$_3$O$_4$, MnFe$_2$O$_4$, and Zn$_{0.2}$Mn$_{0.8}$Fe$_2$O$_4$ was negligible. In EDX, Fe$_3$O$_4$ single phase MNS show only Fe peaks, and Fe$_3$O$_4$/ Zn$_{0.2}$Mn$_{0.8}$Fe$_2$O$_4$ core/shell MNS show the presence of Mn and Zn peaks in addition to Fe peaks, confirming the Zn$_{0.2}$Mn$_{0.8}$Fe$_2$O$_4$ shell coating on Fe$_3$O$_4$ nanoparticles (not shown). A high resolution TEM (HRTEM) image and an SAED pattern of Fe$_3$O$_4$/MnFe$_2$O$_4$MNS were obtained, confirming the crystalline nature of the particle and spinel AB$_2$O$_4$ crystal structure (not shown).

To show the direct evidence of core/shell structure, MNS were characterized via EELS. Elemental analysis was done on a single Fe$_3$O$_4$/MnFe$_2$O$_4$ MNS via core-loss and low loss line scan and area map (not shown). An elemental EELS line scan was done at five different points from edge to center to edge, and the corresponding Fe and Mn intensity peaks were observed. The Fe peak was normalized and compared to the intensity of Mn. At the edges, the intensity of Mn was noticeable, but moving towards center the Mn intensity dropped significantly due to a dominant signal from the Fe$_3$O$_4$ core. Elemental EELS maps of Fe$_3$O$_4$/MiFe$_2$O$_4$MNS were obtained (not shown). In the Fe map, the presence of Fe can be seen throughout the particle, while intensity is higher in the core region than at the edges. However, in the Mn map, Mn is dominant at the edges rather than in the center. Higher Mn signal at the edges compared to the center in both line scan and area maps confirms a uniform MnFe$_2$O$_4$ shell on Fe$_3$O$_4$ nanostructures.

FIGS. 2A-2D show M-H loops of 12 nm single phase and core/shell MNS (set 1 and 2) measured at RT and 10K. At RT, all the core/shell and single phase MNS show no hysteresis and demonstrate superparamagnetic behavior (FIGS. 2A and 2B). For the set 1 samples, saturation magnetization for 12 nm Fe$_3$O$_4$/Zn$_{0.2}$Mn$_{0.8}$Fe$_2$O$_4$ and 12 nm Fe$_3$O$_4$/MnFe$_2$O$_4$ core/shell MNS was found to be 95 emu/g and 86 emu/g, respectively, higher than 12 nm Fe$_3$O$_4$ MNS (76 emu/g). Similarly, for set 2, saturation magnetization of Zn$_{0.2}$Mn$_{0.8}$Fe$_2$O$_4$/Fe$_3$O$_4$ (91 emu/g) and MnFe$_2$O$_4$/Fe$_3$O$_4$ (82 emu/g) core/shell MNS was found to be higher than 12 nm single phase Fe$_3$O$_4$ MNS. In both cases, core/shell MNS with Zn$_{0.2}$Mn$_{0.8}$Fe$_2$O$_4$ showed the highest saturation magnetization, followed by core/shell MNS with MnFe$_2$O$_4$. Single phase Fe$_3$O$_4$ MNS showed the lowest saturation magnetization in sets 1 and 2.

Figure 2C:
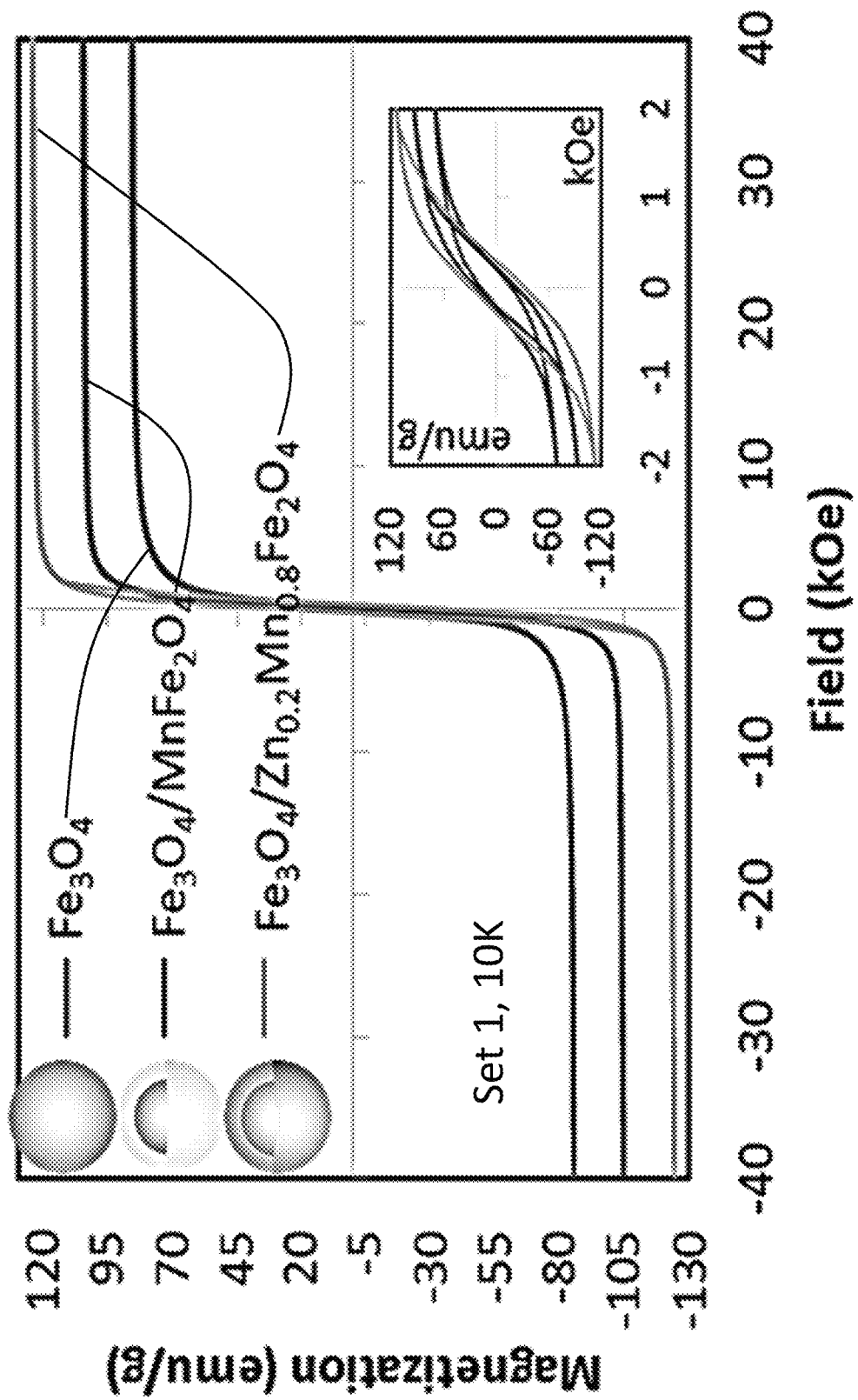
Figure 2D:
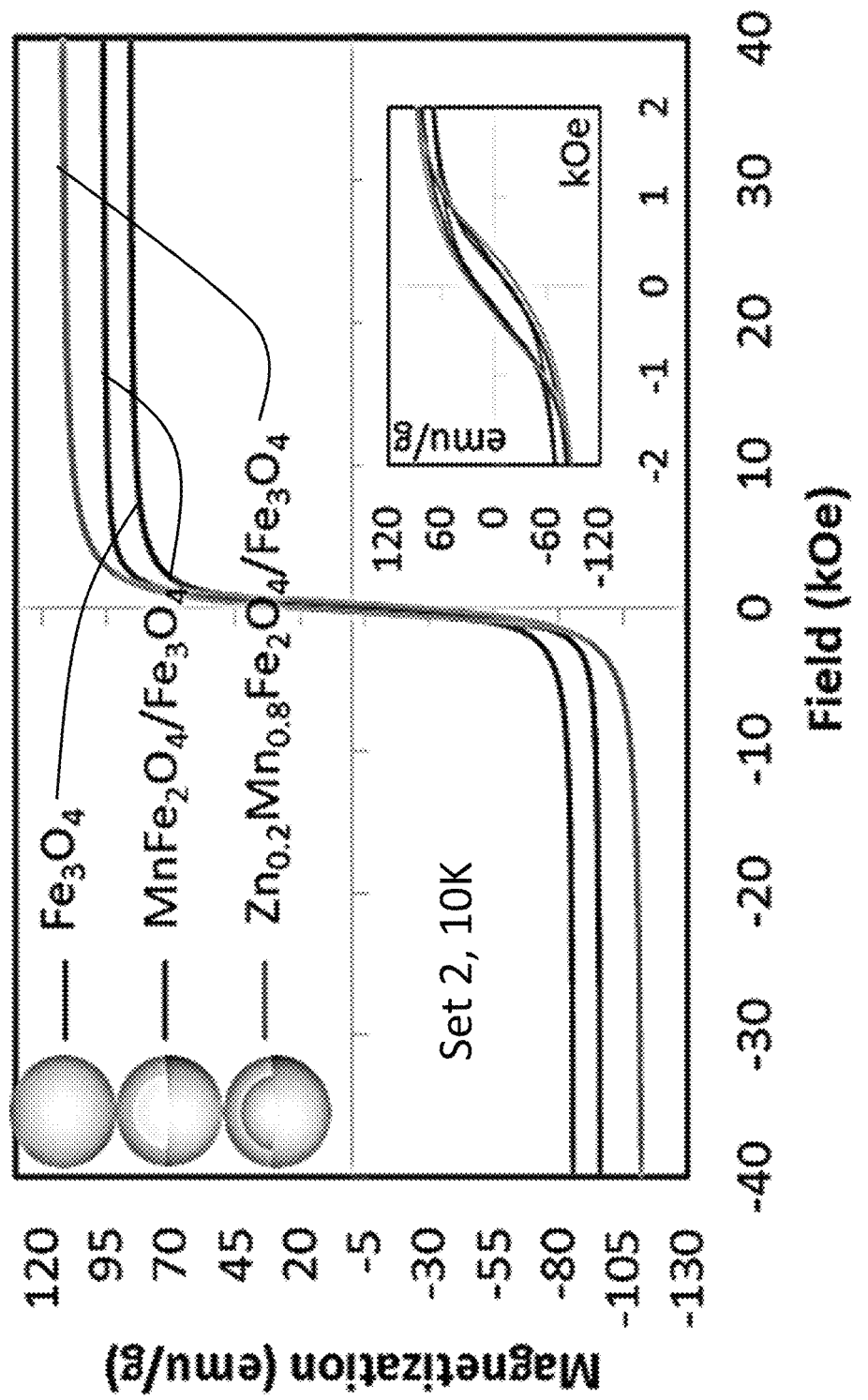

However, when M-H loops of core/shell and single phase MNS were measured at 10K, two key observations were made (FIGS. 2C and 2D). First, the M-H loops measured at 10K showed hysteresis, indicating their ferromagnetic behavior. The saturation magnetization of all the samples (core/shell and single phase MNS) at 10K was observed higher than the saturation magnetization measured at RT. Secondly and more importantly, no kink was observed in the hysteresis loops of all core/shell MNS measured at 10K. It has been observed that when two different ferrite nanoparticles are physically mixed together, it results in a kink in their hysteresis loops due to a lack of exchange interactions between them, resulting in two phase behavior. Although each spinel ferrite showed different magnetic behavior (saturation magnetization, remnant magnetization, and coercivity) at 10K (not shown), the magnetic flux density field (B-H) hysteresis loops of core/shell MNS at RT showed smooth permeability or change in magnetic flux density with field, suggesting intimate contact and exchange-coupling between core and shell ferrite (not shown). These results are evidence of exchange spring behavior.

Figure 3A:
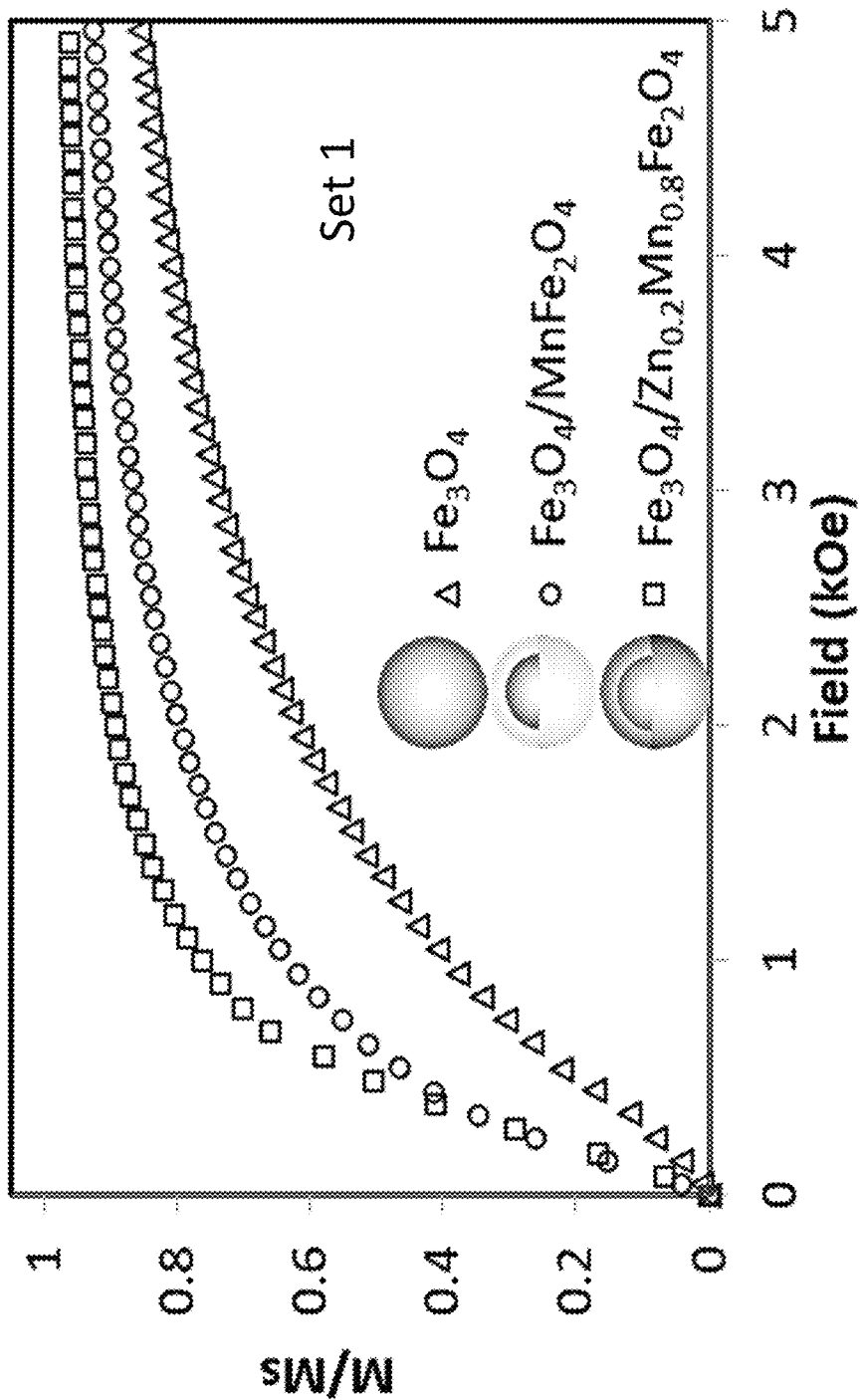
FIG. 3A-3D show normalized magnetic susceptibility plots of set 1 ($Fe_3O_4$, $Fe_3O_4/MnFe_2O_4$, $Fe_3O_4/Zn_{0.2}Mn0.8Fe_2O_4$), set 2 ($Fe_3O_4$, $MnFe_2O_4/Fe_3O_4$, $Zn_{0.2}Mn_{0.8}Fe_2O_4/Fe_3O_4$), set 3 ($Fe_3O_4$, $MnFe_2O_4$, $Fe_3O_4/MnFe_2O_4$, $MnFe_2O_4/Fe_3O_4$), and set 4 ($MnFe_2O_4$, $Zn_{0.2}Mn_{0.8}Fe_2O_4$, $MnFe_2O_4$, $Zn_{0.2}Mn_{0.2}Fe_2O_4$, $Zn_{0.2}Mn_{0.8}$, $Fe_2O_4/MnFe_2O_4$) samples.
Figure 3B:
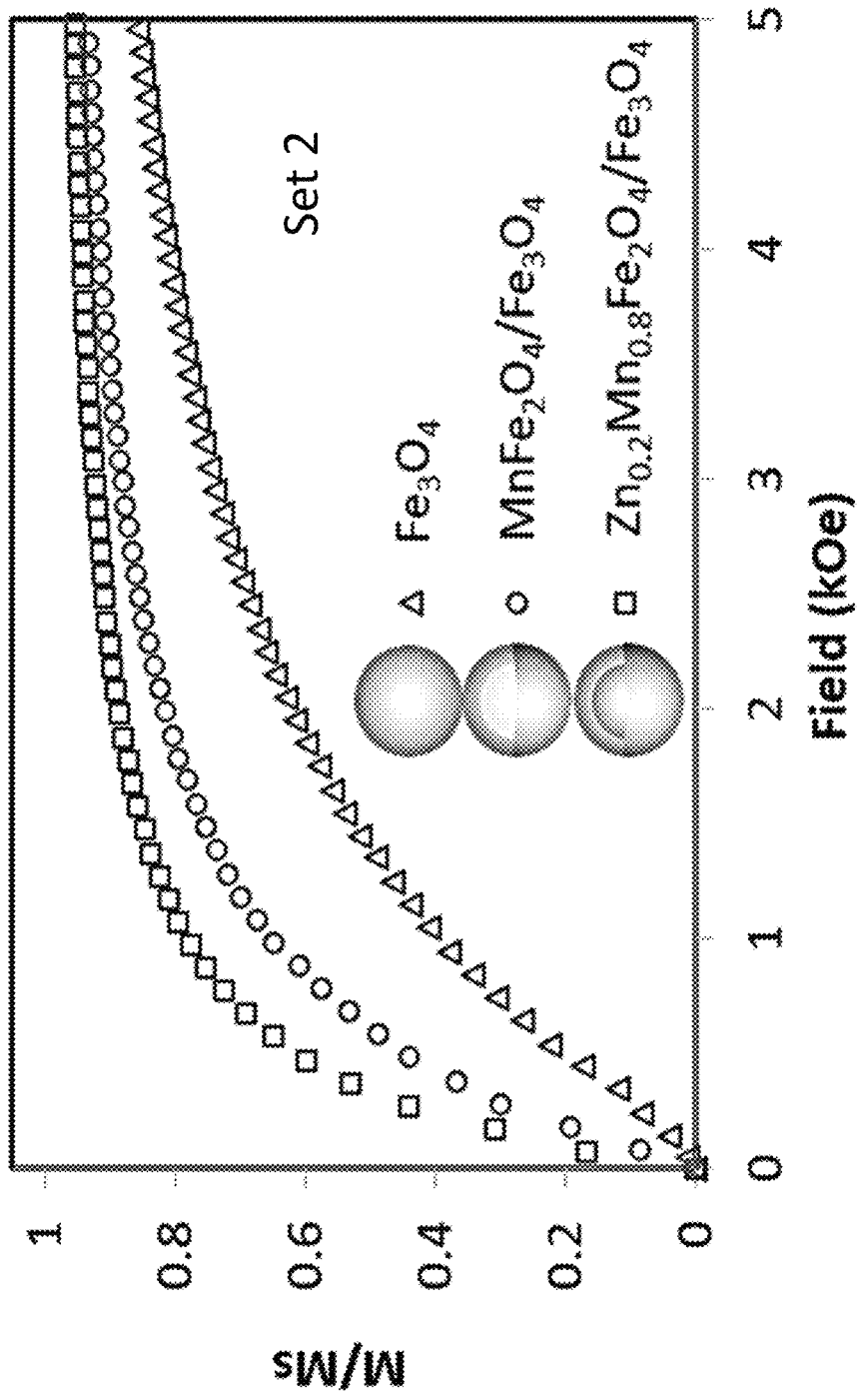
Figure 3C:
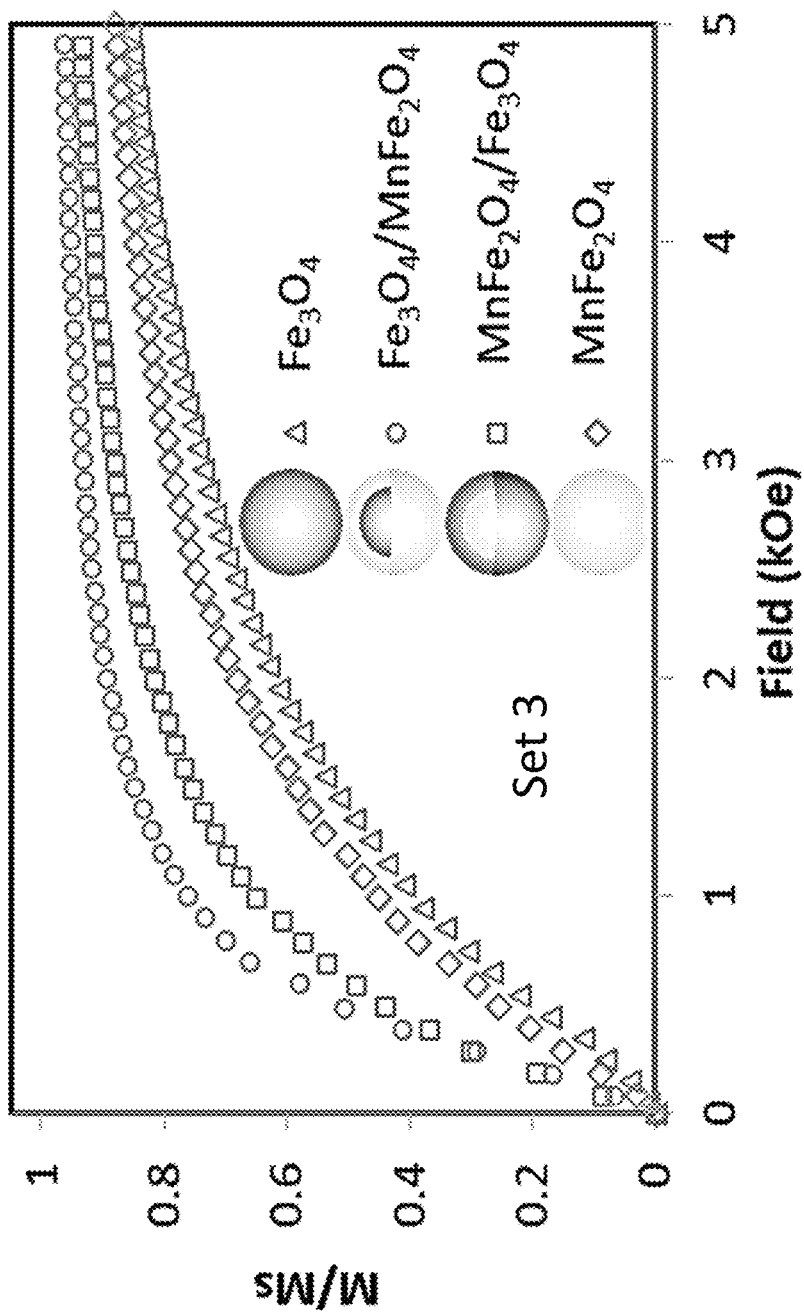
Figure 3D:
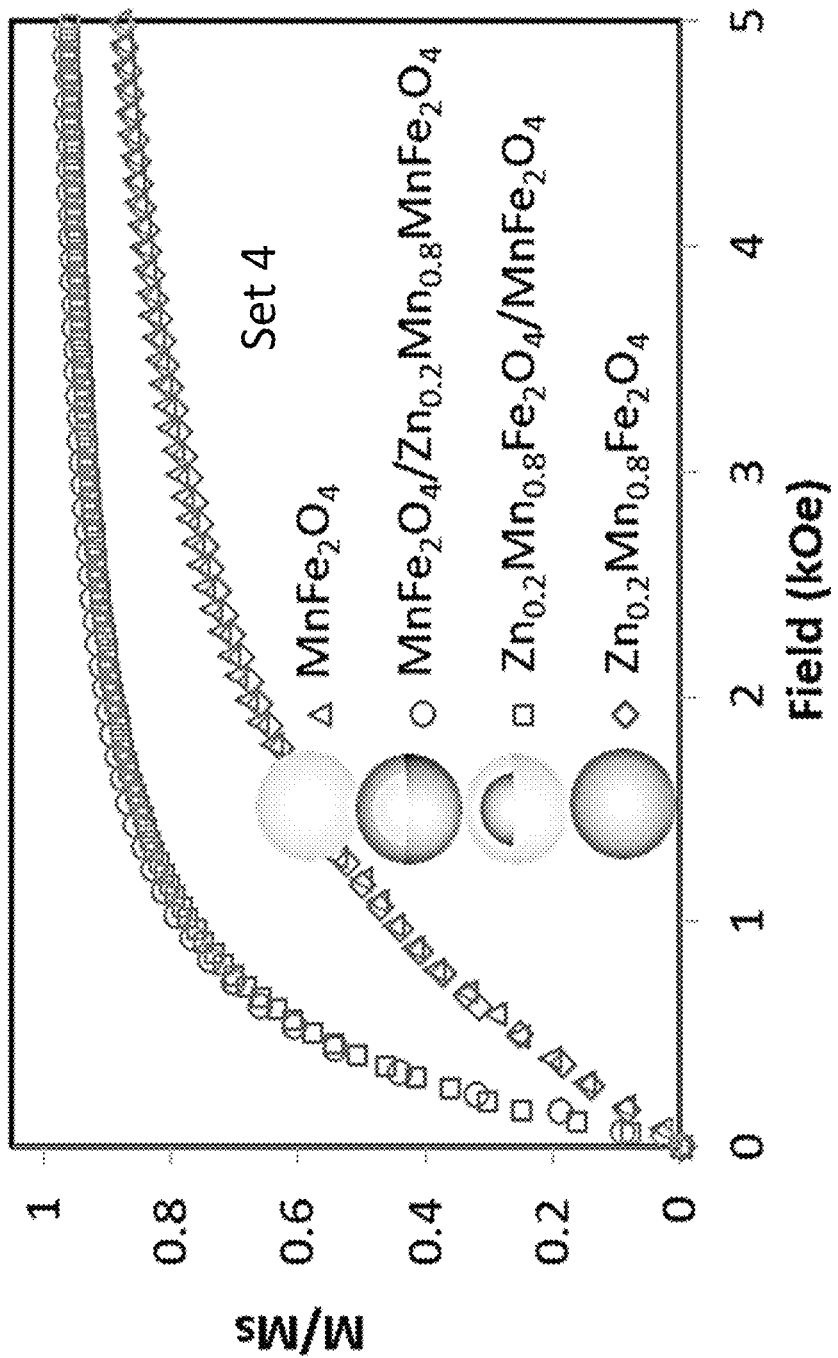

Since it is hard to see any direct effects of exchange coupling on saturation magnetization, susceptibility plots were recorded by measuring magnetization of core/shell and single phase MNS samples at magnetic fields from 0 to 4T at RT. To determine susceptibility independent of saturation magnetization, the susceptibility plots were normalized. For sets 1 and 2, when the core (or shell) was replaced from Fe$_3$O$_4$ to MnFe$_2$O$_4$ and Zn$_{0.2}$Mn$_{0.8}$Fe$_2$O$_4$, an increase in magnetic susceptibility was observed (FIGS. 3A and 3B), In addition to sets 1 and 2, susceptibility of Fe$_3$O$_4$ and MnFe$_2$O$_4$ single phase MNS was compared with their core/shell counterparts, Fe$_3$O$_4$/MnFe$_2$O$_4$ and MnFe$_2$O$_4$/Fe$_3$O$_4$ (set 4 samples). Similarly, MnFe$_2$O$_4$ and Zn$_{0.2}$Mn$_{0.8}$Fe$_2$O$_4$ single phase MNS were compared with MnFe$_2$O$_4$/Zn$_{0.2}$Mn$_{0.8}$Fe$_2$O$_4$ and Zn$_{0.2}$Mn$_{0.8}$Fe$_2$O$_4$/MnFe$_2$O$_4$ (set 4 samples). In both sets 3 and 4, susceptibility of the single phase MNS was observed to be lower than their core/shell counterparts.

Since the M-H loops of both core/shell and single phase MNS show superparamagnetic behavior at RT but ferromagnetic behavior at 10K, their blocking temperature is be between these two temperatures. To measure the blocking temperature, ZFC magnetization plots of core/shell and single phase MNS were collected at 100 Oe (FIGS. 4A-4B), Here, the key result to observe is that all core/shell MNS showed a single peak in ZFC plots, confirming exchange coupling between core and shell ferrites. Blocking temperature of core/shell MNS was found to be significantly higher than single phase MNS. For set 1 samples, when the shell was changed from Fe$_3$O$_4$ to MnFe$_2$O$_4$ and Zn$_{0.2}$Mn$_{0.8}$Fe$_2$O$_4$, blocking temperature increased from 90K to 162K and 265K, respectively (FIG. 4A). Similarly, for set 2 samples, when the core was changed from Fe$_3$O$_4$ to MnFe$_2$O$_4$ and Zn$_{0.2}$Mn$_{0.8}$Fe$_2$O$_4$, blocking temperature increased from 90K to 157K and 222K, respectively (FIG. 4B). Blocking temperature is strongly dependent on the size of the MNS. However, in this case, since the sizes of single phase and core/shell MNS are similar, the higher blocking temperature may be correlated to the higher effective anisotropy of core/shell MNS. Other than shift, broadening of the ZFC peak was also observed in the core/shell MNS samples. Broadening has been correlated with the large size distribution of MNS. However, since the size distribution of the core/shell MNS is very narrow in this case, the broadening may be explained to be due to the increased inter-particle interactions that arise from either dipolar interactions between MNS or the exchange interactions between the magnetic ions at the surface of nanoparticles.

Magnetic nanostructures have been used successfully as T$_2$ contrast agents in magnetic resonance imaging (MRI). The T$_2$ contrast enhancement effect of MNS is measured by r$_2$ relaxivity, a slope of relaxation rate R$_2$ (s$^{-1}$) plotted against MNS metal concentration (mM). The higher relaxivity corresponds to a higher T$_2$ contrast enhancement effect. The R$_2$ relaxation rate of MNS is defined as $$R_2 = \frac{1}{T_2} = \frac{256\pi^2\gamma^2}{405} M_s^2 V \frac{r^2}{D\left(1+\frac{L}{r}\right)} \tag{2}$$

where T$_2$ is transverse relaxation time, $\gamma$ is proton gyromagnetic ratio, M$_s$ is saturation magnetization, V is volume of MNS, D is diffusion coefficient of water molecules, r is radius of MNS core, and L is thickness of MNS surface coating. (Koenig, S. H. et al., *Magn. Meson. Med.* 1995, 34, 227-233.) Based on equation 2, r$_2$ is dependent on saturation magnetization and susceptibility of MNS. In FIGS. 5A-5F, r$_2$ relaxivity values and plots of 12 nm core/shell MNS were compared with the same size single phase MNS. The spin-spin relaxation time (T$_2$) was observed at 3T. Consistent with the magnetization and susceptibility data, core/shell MNS showed higher r$_2$ relaxivity than similarly sized single phase MNS. For the set 1 samples, when the shell was changed from Fe$_3$O$_4$ to MnFe$_2$O$_4$ and Zn$_{0.2}$Mn$_{0.8}$Fe$_2$O$_4$, relaxivity increased from 372 to 427 and 487 mM$^{-1}$s$^{-1}$, respectively (FIG. 5A). Similarly, for set 2 samples, when the core was changed from Fe$_3$O$_4$ to MnFe$_2$O$_4$ and Zn$_{0.2}$Mn$_{0.8}$Fe$_2$O$_4$, SAR increased from 372 to 416 and 457 mM$^{-1}$s$^{-1}$, respectively (FIG. 5B). In both sets, an increase in relaxivity suggested that exchange coupling between Fe$_3$O$_4$ and MnFe$_2$O$_4$ (or Zn$_{0.2}$Mn$_{0.8}$Fe$_2$O$_4$) had an impact on relaxivity. However, it should also be noted that core MnFe$_2$O$_4$ and Zn$_{0.2}$Mn$_{0.8}$Fe$_2$O$_4$ showed higher relaxivity than Fe$_3$O$_4$. One of the reasons for this increasing trend could be the higher relaxivity of MnFe$_2$O$_4$ and Zn$_{0.2}$Mn$_{0.8}$Fe$_2$O$_4$. To observe the direct effect of exchange coupling, r$_2$ relaxivity of Fe$_3$O$_4$ and MnFe$_2$O$_4$ MNS was compared with their core/shell counterparts, Fe$_3$O$_4$/MnFe$_2$O$_4$ and MnFe$_2$O$_4$/Fe$_3$O$_4$(set 3 samples). Similarly, MnFe$_2$O$_4$ and Zn$_{0.2}$Mn$_{0.8}$Fe$_2$O$_4$ MNS were compared with MnFe$_2$O$_4$/Zn$_{0.2}$Mn$_{0.8}$Fe$_2$O$_4$ and Zn$_{0.2}$Mn$_{0.8}$Fe$_2$O$_4$/MnFe$_2$O$_4$ (set 4 samples). For set 3 and 4 samples, higher r$_2$ relaxivity of core/shell MNS compared to single phase MNS confirmed that exchange coupling between two ferrites can result in significantly higher relaxivity in core/shell MNS (FIGS. 5C and 5D). After optimizing the core and shell combination, the highest $r_2$ relaxivity of up to 684 mM$^{-1}$s$^{-1}$ was obtained, which is ~7 times higher than Ferwnoxtran (dextran coated iron oxide nanoparticles), an FDA approved $T_2$ contrast agent for MRI. This means that when used as a contrast agent, the core/shell MNS can generate 7 times higher signal than Ferumoxtran, or if the signal is already sufficient, administration dosages can be decreased by 7 times.

MNS can he thermally activated and generate heat under an external RF field that makes the MNS unique for non-invasive therapeutic applications in biomedicine. Rosensweig described the analytical relationships and computational models of thermal activation in a suspension of MNS under an external RF field. (Rosensweig, R. E., *J. Magn. Magri. Mater.* 2002, 252, 370-374.) Thermal activation of the MNS under an external RF field is quantified as SAR that is the amount of heat generated per unit gram of the MNS. Higher SAR is critical in order to obtain high therapeutic efficacy of MNS in biomedical applications. The SAR for monodisperse magnetic nanostructures under an external RF field can be calculated as $$SAR \propto m_s^2 H_0^2 fV \frac{2\pi f \tau}{1 + (2\pi f \tau)^2} \quad (3)$$

where $H_0$ is the magnetic field intensity, f is frequency, $m_s$ is saturation magnetization of MNS, V is MNS volume, is effective relaxation time and depends on Brownian ($\tau_B$), and Neel ($\tau_N$) relaxation time as given by $$\frac{1}{\tau} = \frac{1}{\tau_B} + \frac{1}{\tau_N}. \quad (4)$$

The dominant mechanism is the one which has shortest relaxation time. If $\tau_B \ll \tau_N$ then $\tau = \tau_B$, while if $\tau_B \gg \tau_N$ then $\tau = \tau_N$. In superparamagnetic nanoparticles of sizes smaller than 16 nm, $\tau_B \gg \tau_N$, so heating mainly arises due to Néel relaxation which can be calculated as $$\tau_N = \tau_0 \exp\left(\frac{K_u V_m}{k_B T}\right) \quad (5)$$

where $\tau_0$ is constant, $K_u$ is anisotropic constant of MNS, $V_m$ is volume of MNS, $k_B$ is Boltzmann's constant, and T is temperature. According to equations (3) and (5), the SAR depends on many factors. For the experiments described here, factors such as $H_0$, f, and V are constant, and magnetization and anisotropy are the contributing factors for SAR. FIGS. 6A-6F show the thermal activation plots and SAR values of core/shell and single phase MNS under RF field of 5 kA/m (5 kW, 300 kHz). The field ($H_0$) and frequency (f) was chosen such that the $H_0$f factor was well below the experimentally estimated threshold of $5 \times 10^9$ A/ms. The concentration of both core/shell and single phase MNS was kept the same to avoid any concentration dependence effects on SAR. Consistent with anisotropy and magnetization data, the calculated SAR values based on the thermal activation plots show that core/shell MNS possess superior thermal activation properties over single phase MNS (FIG. 6A). For set 1 samples, when the shell was changed from $Fe_3O_4$ to $MnFe_2O_4$ and $Zn_{0.2}Mn_{0.8}Fe_2O_4$, SAR increased from 93 to 405 and 427 W/g, respectively. Similarly, for set 2 samples, when the core was changed from $Fe_3O_4$ to $MnFe_2O_4$ and $Zn_{0.2}Mn_{0.8}Fe_2O_4$, SAR increased from 93 to 172 and 223 W/g, respectively. As the core (or shell) component was replaced from $Fe_3O_4$ to $MnFe_2O_4$ and $Zn_{0.2}Mn_{0.8}Fe_2O_4$, the exchange coupling due to the difference in anisotropy between core and shell caused higher thermal activation and hence higher SAR.

Figure 6B:
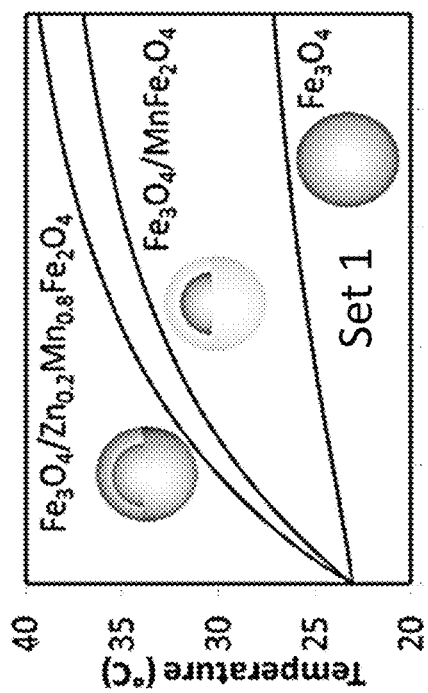
Figure 6E:
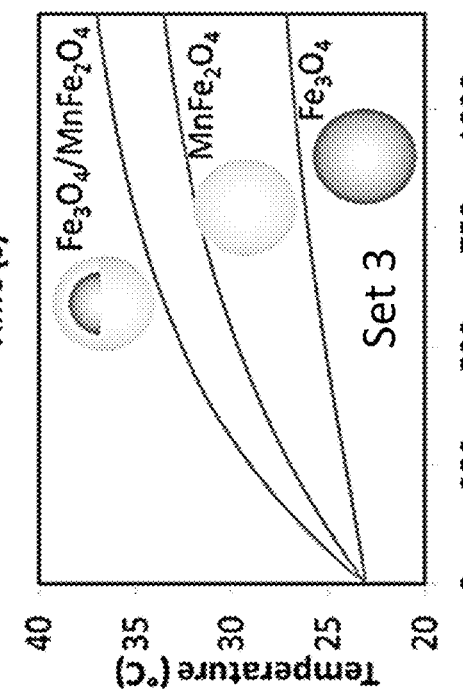

Similar to $r_2$ relaxivity, SAR of 12 nm $Fe_3O_4/MnFe_2O_4$ MNS was compared with 12 nm $Fe_3O_4$ and 12 nm $MnFe_2O_4$ (set 3 samples). The SAR value of 12 nm $Fe_3O_4/MnFe_2O_4$ core/shell MNS was found to be 405 W/g, 1.5 times higher than 12 nm $MnFe_2O_4$ (269 W/g) and around 4.5 times higher than 12 nm $Fe_3O_4$ nanostructures (93 W/g) (FIG. 6B). A similar trend was observed for $MnFe_2O_4/Zn_{0.2}Mn_{0.8}Fe_2O_4$ core/shell MNS over 12 nm $MnFe_2O_4$ and 12 nm $Zn_{0.2}Mn_{0.8}Fe_2O_4$ nanoparticles (set 4 samples). After optimizing the core and shell combination, the highest SAR up to 748 W/g was obtained. This change in SAR suggests that for core/shell MNS, exchange coupling can enhance anisotropy that directly affects their thermal activation properties. Overall, it has been shown here that by just changing the morphology from single phase to core/shell and controlling composition, RF field induced heating temperatures can be increased from 26° C. to the temperature range that is considered ideal for targeted therapy (43-47° C.). For diseases such as cancer, MNS under application of RF field can specifically kill cancer cells at these temperatures without affecting any normal cells, thus making the treatment non-invasive and without any side effects.

Figures 7B, 7C:
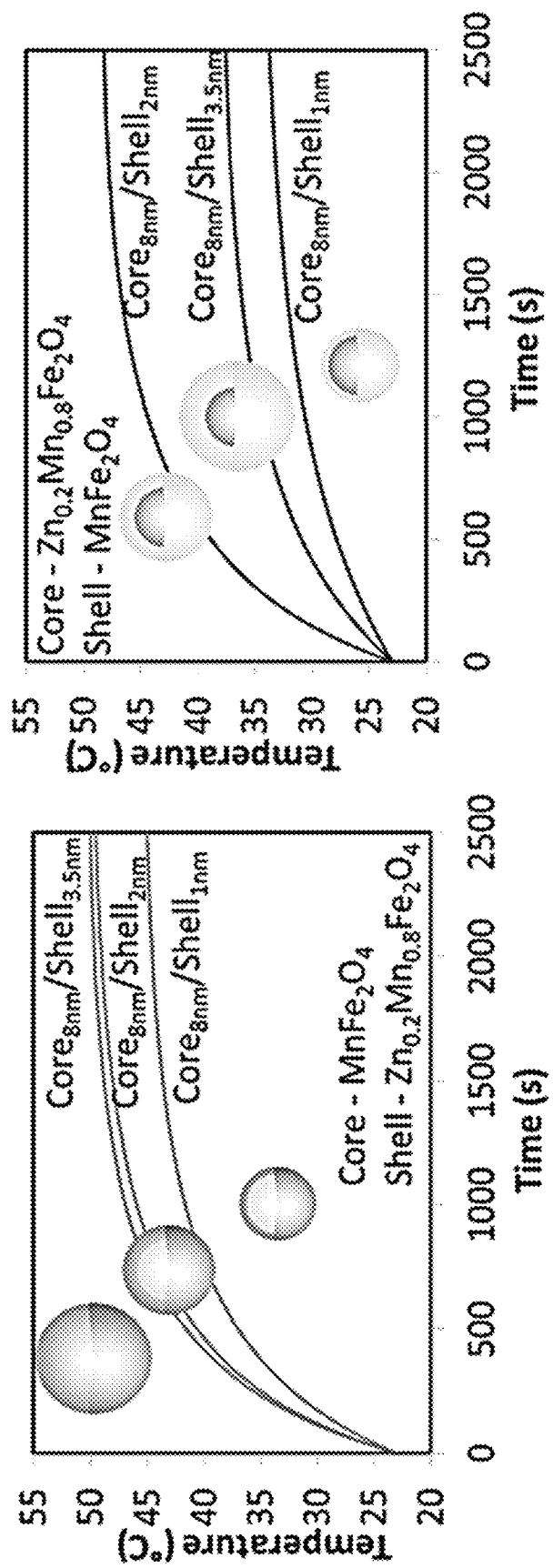

The Here, the thermal activation properties of core/shell MNS were further optimized by tuning dimension and ratio of core and shell components. Core/shell MNS with 8 nm core with 1, 2, and 3.5 nm shell thickness were prepared, resulting in particle diameter 10, 12, and 15 nm (TEM images not shown). $MnFe_2O_4$ and $Zn_{0.2}Mn_{0.8}Fe_2O_4$ as core and shell (or vice versa) were selected for the study due to their higher theranostic properties among all core/shell combinations. For both sets, the thermal activation properties of the core/shell MNS changed significantly when the shell thickness was tuned from 1 to 3.5 nm (FIGS. 7A-7C). When $Zn_{0.2}Mn_{0.8}Fe_2O_4$ core was kept constant, RF heating temperature increased first when the $MnFe_2O_4$ shell thickness was increased from 1 to 2 nm. When the shell thickness was further increased to 3.5 nm, the RF heating temperature reduced (FIG. 7B). Since anisotropy of $MnFe_2O_4$ is lower than $Zn_{0.2}Mn_{0.8}Fe_2O_4$, exceedingly higher amounts (3.5 nm shell) of $MnFe_2O_4$ can result in overall lower anisotropy of core/shell MNS, resulting in a decrease in RF heating temperature. When $MnFe_2O_4$ core was kept constant and $Zn_{0.2}Mn_{0.8}Fe_2O_4$ shell thickness was tuned, RF heating temperature increased first when the shell thickness was increased from 1 to 2 nm and then stayed almost same when the shell thickness was further increased to 3.5 nm (FIG. 7C). By just interchanging core and shell materials, a different trend was observed since the proportion of high and low anisotropic phases changed, indicating that exchange coupling is also significantly dependent on proportion of each ferrite. After the optimization process, the highest SAR up to 827 W/g was obtained that was ~9 times higher than single phase $Fe_3O_4$ MNS. These results indicate that an optimum dimension and proportion of core and shell components can provide a maximum exchange coupling.

Conclusions

Exchange coupling in core/shell MNS where both core and shell components are composed of soft magnetic ferrites ($Fe_3O_4$, $MnFe_2O_4$, $Zn_{0.2}Mn_{0.8}Fe_2O_4$) has been demonstrated. Direct effect of exchange coupling was observed by comparison of physical properties of core/shell MNS with their single-phase counterparts of the same size. Due to exchange coupling, higher magnetic susceptibility and anisotropy were observed in core/shell MNS compared to the single-phase counterparts. As a result, $r_2$ relaxivity was doubled in core/shell MNS that resulted in values up to 684 $mM^{-1}s^{-1}$, 7 times higher than the FDA approved $T_2$ contrast agent Ferumoxtran. SAR up to 827 W/g was obtained from core/shell MNS that was almost 9 times higher than conventional ferrite based MNS. The findings described here present exchange coupling as an alternative approach to improve theranostic properties of biocompatible and soft magnetic ferrite based MNS. Due to their biocompatibility and excellent theranostic properties, exchange-coupled core/shell MNS find use in diagnostic imaging and drug delivery applications The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the invention to enable one skilled in the art to utilize the disclosure in various embodiments and with various modifications as suited to the particular use contemplated. It is intended that the scope of tare disclosure be defined by the claims appended hereto and their equivalents.

What is claimed is:

1. A superparamagnetic nanocomposite comprising a superparamagnetic core comprising a first, soft superparamagnetic ferrite and a superparamagnetic shell comprising a second, soft superparamagnetic ferrite, the shell formed over the core, wherein the first and second soft superparamagnetic ferrites are different compounds and have different magnetocrystalline anisotropies, wherein the first soft superparamagnetic ferrite is $MnFe_2O_4$ and the second soft superparamagnetic ferrite is $Zn_{0.2}Mn_{0.8}Fe_2O_4$ or the first soft superparamagnetic ferrite is $Zn_{0.2}Mn_{0.8}Fe_2O_4$ and the second soft superparamagnetic ferrite is $MnFe_2O_4$.

2. The superparamagnetic nanocomposite of claim 1, wherein a sample of nanoparticles composed of the first, soft superparamagnetic ferrite and having an average diameter of 12 nm provides a magnetization-field loop exhibiting no hysteresis at room temperature and a single-peaked zero-field cooling curve having a blocking temperature of less than room temperature.

3. The superparamagnetic nanocomposite of claim 1, wherein the nanocomposite is characterized by a specific absorption rate of at least 300 W/g.

4. The superparamagnetic nanocomposite of claim 1, wherein the nanocomposite is characterized by a specific absorption rate of at least 600 W/g.

5. The superparamagnetic nanocomposite of claim 1, wherein the first soft superparamagnetic ferrite is $MnFe_2O_4$ and the second soft superparamagnetic ferrite is $Zn_{0.2}Mn_{0.8}Fe_2O_4$.

6. The superparamagnetic nanocomposite of claim 1, wherein the first soft superparamagnetic ferrite is $Zn_{0.2}Mn_{0.8}Fe_2O_4$ and the second soft superparamagnetic ferrite is $MnFe_2O_4$.

7. The superparamagnetic nanocomposite of claim 1, wherein the nanocomposite is free of Co, Pt, Nd, and Sm.

8. The superparamagnetic nanocomposite of claim 1, wherein the nanocomposite is a nanoparticle.

9. A composition comprising the superparamagnetic nanocomposite of claim 1 and a carrier.

10. A method comprising delivering the superparamagnetic nanocomposite of claim 1 to a patient and exposing the nanocomposite to a magnetic field.

11. A method comprising delivering the superparamagnetic nanocomposite of claim 1 to a patient and exposing the nanocomposite to an external radio frequency field.

* * * * *